(12) United States Patent
Tanabe et al.

(10) Patent No.: US 9,895,047 B2
(45) Date of Patent: Feb. 20, 2018

(54) IMAGE PICKUP APPARATUS

(71) Applicant: OLYMPUS CORPORATION, Tokyo (JP)

(72) Inventors: Yuzuru Tanabe, Niiza (JP); Shinji Yamashita, Tachikawa (JP); Yasunori Matsui, Hino (JP); Yuta Matsuno, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/479,838

(22) Filed: Apr. 5, 2017

(65) Prior Publication Data

US 2017/0209023 A1 Jul. 27, 2017

Related U.S. Application Data

(63) Continuation of application No. PCT/JP2016/067816, filed on Jun. 15, 2016.

(30) Foreign Application Priority Data

Jul. 22, 2015 (JP) .................................. 2015-145093

(51) Int. Cl.
*A62B 1/04* (2006.01)
*H04N 9/47* (2006.01)
(Continued)

(52) U.S. Cl.
CPC ...... *A61B 1/00009* (2013.01); *A61B 1/00045* (2013.01); *A61B 1/04* (2013.01);
(Continued)

(58) Field of Classification Search
None
See application file for complete search history.

(56) References Cited

U.S. PATENT DOCUMENTS

2009/0216080 A1 8/2009 Nakamura
2014/0163319 A1* 6/2014 Blanquart ............ A61B 1/0638
600/109
(Continued)

FOREIGN PATENT DOCUMENTS

EP 2 094 002 A2 8/2009
JP 9-83840 A 3/1997
(Continued)

OTHER PUBLICATIONS

International Search Report dated Sep. 6, 2016 received in PCT/JP2016/067816.

*Primary Examiner* — Talha M Nawaz
(74) *Attorney, Agent, or Firm* — Scully, Scott, Murphy & Presser, P.C.

(57) ABSTRACT

An image pickup apparatus includes a solid state image pickup device including a plurality of pixels with a photoelectric conversion element, a transfer section, an electric charge conversion section, a reset section, an operation mode control section configured to switch a first operation mode in which the reset section and the transfer section are turned off, and a second operation mode in which the reset section is turned off, and the transfer section is turned on, a black level correction section, and a memory, and transfers a synchronous signal for outputting an image signal from the solid state image pickup device, and a control signal for causing the solid state image pickup device to operate in the first operation mode and the second operation mode respectively by using a common signal line.

7 Claims, 14 Drawing Sheets

(51) Int. Cl.
  *H04N 7/18* (2006.01)
  *A61B 1/00* (2006.01)
  *A61B 1/04* (2006.01)
  *A61B 1/06* (2006.01)
  *G02B 23/24* (2006.01)
  *H04N 5/232* (2006.01)
  *H04N 5/243* (2006.01)
  *H04N 5/374* (2011.01)
  *H04N 5/367* (2011.01)
  *H04N 5/225* (2006.01)

(52) U.S. Cl.
  CPC ........ *A61B 1/0676* (2013.01); *G02B 23/2484* (2013.01); *H04N 5/23245* (2013.01); *H04N 5/243* (2013.01); *H04N 5/367* (2013.01); *H04N 5/374* (2013.01); *H04N 2005/2255* (2013.01)

(56) References Cited

U.S. PATENT DOCUMENTS

| | | | |
|---|---|---|---|
| 2014/0267654 A1* | 9/2014 | Blanquart | H04N 5/365 348/65 |
| 2014/0340496 A1* | 11/2014 | Okawa | A61B 1/00006 348/65 |
| 2016/0174811 A1* | 6/2016 | Saito | A61B 1/00009 600/109 |

FOREIGN PATENT DOCUMENTS

| | | |
|---|---|---|
| JP | 2007-19577 A | 1/2007 |
| JP | 2009-195602 A | 9/2009 |
| JP | 2010-56723 A | 3/2010 |
| JP | 2010-171925 A | 8/2010 |
| JP | 2010-193042 A | 9/2010 |
| JP | 2013-219558 A | 10/2013 |
| JP | 2014-82698 A | 5/2014 |
| JP | 2014-138356 A | 7/2014 |

* cited by examiner

IMAGE PICKUP APPARATUS

CROSS REFERENCE TO RELATED APPLICATION

This application is a continuation application of PCT/JP2016/067816 filed on Jun. 15, 2016 and claims benefit of Japanese Application No. 2015-145093 filed in Japan on Jul. 22, 2015, the entire contents of which are incorporated herein by this reference.

BACKGROUND OF INVENTION

1. Field of the Invention

The present invention relates to an image pickup apparatus that picks up an image by using a solid state image pickup device.

2. Description of the Related Art

In recent years, image pickup apparatuses using solid state image pickup devices have been widely used in various apparatuses including the case of medical endoscopes.

In the case of a medical endoscope that is inserted into a body cavity, it is necessary to achieve diameter reduction to reduce a pain given to a patient by reducing an outside diameter of an insertion portion that is inserted into the body cavity, and it becomes necessary to reduce a size of a solid state image pickup device that is disposed in a distal end portion of the insertion portion.

In order to reduce the size of the solid state image pickup device which is disposed in the distal end portion of the insertion portion, it is conceivable to configure some pixels at a peripheral side of pixels forming a light receiving portion to have a configuration of effective pixels having no optical black pixels (OB pixels) that generate signals of black levels on an picked-up image by mechanically blocking light from reaching some pixels at the peripheral side of the pixels forming the light receiving section.

Although it becomes possible to reduce the size of the solid state image pickup device which is disposed in the distal end portion of the insertion portion by adopting the solid state image pickup device having no OB pixels in this way, the black levels on the picked-up image is in an indefinite state by adopting the configuration having no OB pixels, and the entire image becomes white (black floating) or becomes unnatural black (black sinking) on monitor display, so that a circuit configuration that generates signals of black levels is needed.

For example, Japanese Patent Application Laid-Open Publication No. 2007-019577 as a first prior example discloses an image pickup apparatus including a mechanical shutter configured to capture an object optical image, an image pickup device configured to output an image signal based on the object optical image incident through the mechanical shutter, storage means configured to hold the output from the image pickup device in a light shielding state time by the shutter as a dark output, and correction means configured to estimate noise components in an actual photographing time based on an exposure time period at the actual photographing time at which the object optical image is captured through the mechanical shutter, and the dark output stored in the storage means, and remove the estimated noise components from the output of the image pickup device at the actual photographing time to output the output of the image pickup device.

Further, Japanese Patent Application Laid-Open Publication No. 2014-82698 as a second prior example discloses an image pickup apparatus including an image pickup device capable of acquiring a first photographed image and a second photographed image in one image output period, image judging means configured to judge whether or not to acquire an image for dark shading correction in accordance with photographing conditions, image acquisition means configured to acquire the image for dark shading correction instead of the second photographed image when the image judging means judges to acquire the image for dark shading correction, and image correction means configured to correct the first photographed image and the second photographed image by using the image for dark shading correction.

SUMMARY OF THE INVENTION

An image pickup apparatus of one aspect of the present invention is an image pickup apparatus including an endoscope provided with, at a distal end portion of an insertion portion, a solid state image pickup device including a plurality of pixels with, as a unit pixel, a photoelectric conversion element configured to perform photoelectric conversion corresponding to a light reception amount, and accumulate electric charges, a transfer section configured to transfer the electric charges accumulated in the photoelectric conversion element, an electric charge conversion section configured to convert the electric charges which are transferred, into a signal, a reset section configured to reset the signal of the electric charge conversion section, a signal output section configured to output the signal converted by the electric charge conversion section, and a vertical transfer line connected to the signal output section, and a signal processing apparatus including a setting section configured to set operation timings of a first operation mode of outputting a pixel signal of a black level as a result of a signal level of the electric charge conversion section being made the black level by bringing the reset section into an off state, and bringing the transfer section into an off state to the vertical transfer line, and a second operation mode of transferring the electric charges accumulated by the photoelectric conversion element to the electric charge conversion section by bringing the reset section into the off state from an on state, and bringing the transfer section into an on state, and thereafter outputting the signal of the electric charge conversion section to the vertical transfer line via the signal output section as an ordinary pixel signal in which a black level is not corrected, an operation mode control section configured to switch the first operation mode and the second operation mode, and a black level correction section configured to correct black levels in an image signal formed of the ordinary pixel signal in plurality that are outputted from an output section of the solid state image pickup device in the second operation mode, wherein the signal processing apparatus holds pixel signal values of black levels acquired in the first operation mode in a memory, and corrects the image signal acquired in the second operation mode in the black level correction section by using the pixel signal values of the black levels held in the memory, and the image pickup apparatus, as signal lines inserted through an inside of the insertion portion, and configured to transmit a synchronous signal for generating a drive signal for causing the image signal to be outputted from the solid state image pickup device, an operation mode control signal for causing the solid state image pickup device to operate in the first operation mode and the second operation mode respectively, and the image signal, transmits the synchronous signal and the operation mode control signal with use of a common signal line.

DETAILED DESCRIPTION OF THE PREFERRED EMBODIMENT(S)

Hereinafter, an embodiment of the present invention will be described with reference to the drawings.

First Embodiment

Figure 1:
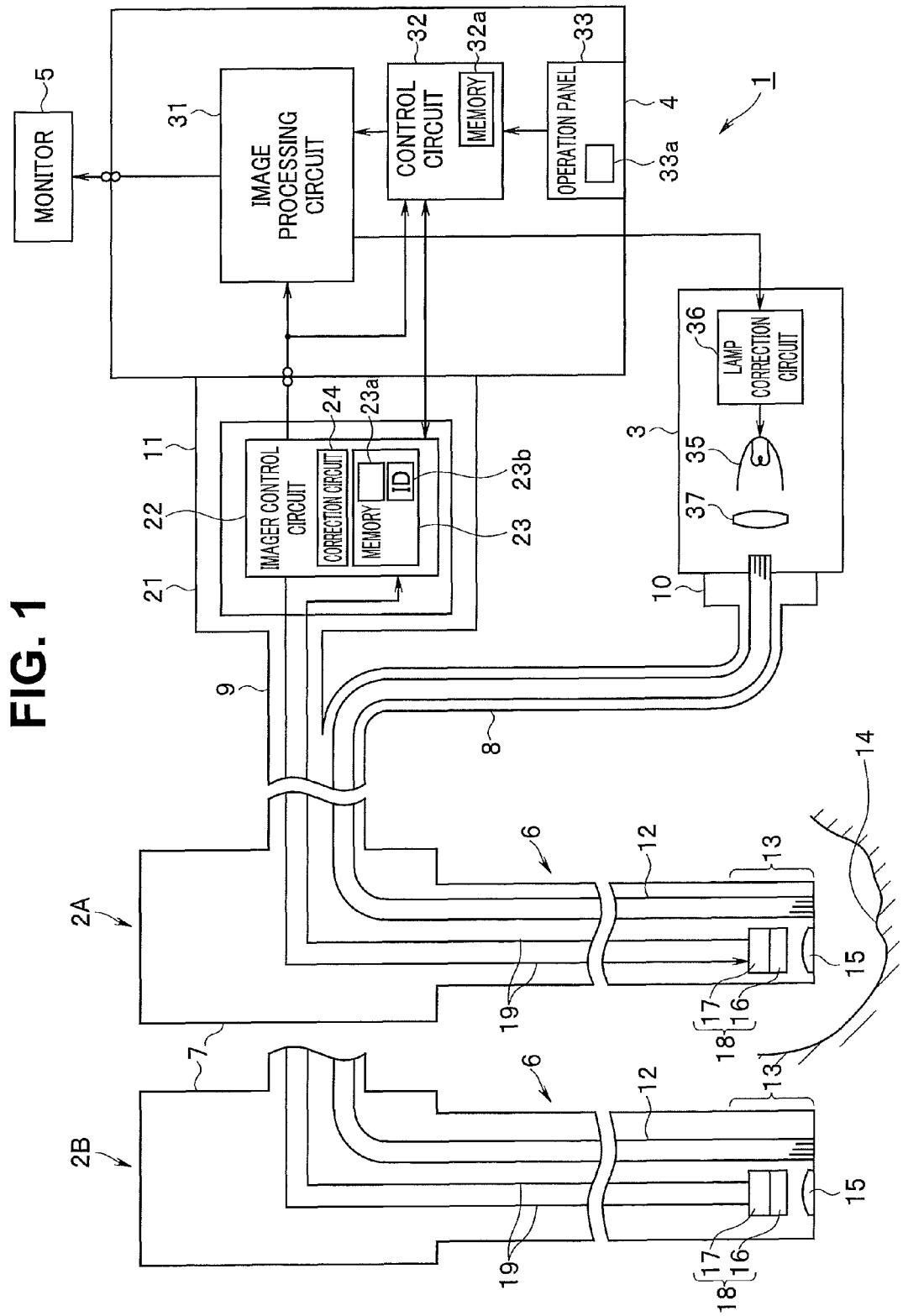
FIG. 1 is a diagram illustrating an entire configuration of an image pickup apparatus of a first embodiment of the present invention.

As illustrated in FIG. 1, an image pickup apparatus 1 of a first embodiment of the present invention includes an endoscope 2A configured to be inserted into a body cavity, a light source apparatus 3 configured to supply illuminating light to the endoscope 2A that is connected attachably and detachably, an image signal processing apparatus 4 configured to perform signal processing to the endoscope 2A that is connected attachably and detachably, and a monitor 5 as a display apparatus configured to display an image of an image signal as an endoscopic image by receiving the image signal for display that is outputted from the image signal processing apparatus 4.

The endoscope 2A includes an elongated insertion portion 6 configured to be inserted into a body cavity, an operation portion 7 that is provided at a proximal end of the insertion portion 6, and a light guide cable 8 and a signal cable 9 that are extended from the operation portion 7. A light source connector 10 provided at an end portion of the light guide cable 8 is connected to the light source apparatus 3 attachably and detachably, and a signal connector 11 provided at an end portion of the signal cable 9 is connected to the image signal processing apparatus 4 attachably and detachably. Note that a structure may be adopted, that integrates the light guide cable 8 and the signal cable 9, extends the signal cable 9 from the light source connector 10 to connect the signal connector 11 at the end portion of the signal cable 9 to the image signal processing apparatus 4, for example.

Note that the image pickup apparatus 1 of the first embodiment may be configured by using an endoscope 2B in which a part of the configuration slightly differs, besides the endoscope 2A. The endoscope 2B includes the insertion portion 6 with a small diameter, but the endoscope 2A includes the insertion portion 6 that is reduced in diameter more than the endoscope 2B. In the endoscope 2A, a number of signal lines that are inserted into the insertion portion 6 is reduced more than in a case of the endoscope 2B, in order to reduce the diameter of the insertion portion 6. Further, in order to reduce the number of signal lines, in the endoscope 2A, a part of a signal processing system is made to have a configuration different from the configuration of the endoscope 2B (refer to FIG. 4 and FIG. 5). In the other respects, the endoscopes 2A and 2B are of the same configuration. Note that in FIG. 1, an internal configuration of the endoscope 2B is of the same configuration as an internal configuration of the endoscope 2A, at a configuration level illustrated in FIG. 1.

A light guide 12 configured to transmit (guide) illuminating light is inserted through an inside of the insertion portion 6 of the endoscope 2A, and the light guide 12 is further inserted through the operation portion 7 and an inside of the light guide cable 8 to reach an end portion of the light source connector 10.

Illuminating light from the light source apparatus 3 is incident on the end portion, and the illuminating light transmitted by the light guide 12 is emitted to an outside from a distal end surface of the light guide 12, that is fixed to an illumination window provided at a distal end portion 13 of the insertion portion 6, and illuminates an observation target site such as an affected part 14 in a body cavity.

The illuminated observation target site forms an optical image of the observation target site on an image pickup surface of a MOS type image pickup device 16 that forms a solid state image pickup device disposed in an image formation position, by an objective lens 15 attached to an observation window that is provided adjacently to the illumination window in the distal end portion 13.

The MOS type image pickup device 16 photoelectrically converts the optical image formed on the image pickup surface by photoelectric conversion elements that form a light receiving section 45 (refer to FIG. 4) disposed on the image pickup surface. An image pickup device control circuit 17 configured to generate a drive signal that drives the MOS type image pickup device 16 and perform control of causing the MOS type image pickup device 16 to operate in two operation modes is disposed in a vicinity of the MOS type image pickup device 16, and a MOS type imager (hereinafter, simply referred to as an imager) 18 is formed of the MOS type image pickup device 16 and the image pickup device control circuit 17.

The imager 18 which is disposed in the distal end portion 13 is connected to an imager control circuit 22 mounted on a scope substrate 21 that is provided inside the signal connector 11 via a plurality of signal lines 19 that are inserted through the insertion portion 6, the operation portion 7 and an inside of the signal cable 9. Note that the scope substrate 21 is not limited to a case where the scope substrate 21 is provided inside the signal connector 11, but a configuration may be adopted, in which the scope substrate 21 is provided inside the operation portion 7, for example. Further, a part of the imager control circuit 22 that is provided inside the scope substrate 21 may be provided inside the image signal processing apparatus 4, and a part of a function of the image signal processing apparatus 4 may be provided in the imager control circuit 22.

The imager control circuit 22 includes a memory 23 including a signal value storage section (or a black level correcting data storage section) 23a configured to store (hold) pixel signal values (also simply referred to as signal values) for correcting black levels of the MOS type image pickup device 16 by controlling the imager 18, and causing the MOS type image pickup device 16 to operate in two operation modes, and a correction circuit 24 forming a black level correction section configured to perform correction of black levels by using the held pixel signal values (or the black level correcting data).

The memory 23 includes an ID storage section 23b (abbreviated as ID in FIG. 1) that stores identification information (abbreviated as ID) peculiar to an endoscope 2K (K=A or B) containing the memory 23.

The image signal processing apparatus 4 to which the signal connector 11 is connected includes an image processing circuit 31 configured to perform signal processing to an image signal outputted from the imager control circuit 22 by being connected to the imager control circuit 22, a control circuit 32 configured to control the imager control circuit 22 and the image processing circuit 31, and an operation panel 33 configured to perform inputs of various settings, conditions for setting and the like to the control circuit 32.

The control circuit 32 reads the ID in the ID storage section 23b, and thereby performs control corresponding to the endoscope 2A or 2B of the ID.

Note that a function of a setting section 33a is provided, which is configured to perform setting of timing and conditions for causing the MOS type image pickup device 16 to operate in the two operation modes by operating the operation panel 33 so as to easily perform adjustment, maintenance and the like of the endoscopes 2A and 2B. When there is no possibility of an ordinary user such as a surgeon causing the MOS type image pickup device 16 to operate in the two operation modes, the setting section 33a may be caused to function only when a specific authentication code that is set on a maker side, for example, is inputted. In the following explanation, explanation will be made by using a user, with a case included, in which only a staff member on the maker side performs operation.

Further, the control circuit 32 includes a memory 32a inside the control circuit 32, for example, and information on the timing and conditions for performing the two operation modes that are set from the setting section 33a or the like is stored in the memory 32a.

In the present embodiment, the MOS type image pickup device 16 is enabled to be driven by switching a first operation mode that causes signals of black levels of respective pixels in the MOS type image pickup device 16 to be outputted, and a second operation mode that causes signals photoelectrically converted in accordance with light receiving amounts received in the respective pixels as will be described later.

The control circuit 32 controls the operation of the MOS type image pickup device 16 in accordance with information on timing or timing conditions for performing the first operation in particular, in the two operation modes stored in the memory 32a. Note that the memory 32a may be configured to be provided outside the control circuit 32. Further, when an instruction to perform the first operation mode is inputted from the operation panel 33 during the second operation mode, for example, the control circuit 32 performs control to cause the MOS type image pickup device 16 and the like to operate by switching the operation mode to the first operation mode even during the second operation mode. Further, as will be described later, when the operation mode of the MOS type image pickup device 16, processing associated with the operation mode and the like are switched, the control circuit 32 performs switch via the imager control circuit 22, and the image pickup device control circuit 17 in the imager 18.

The image processing circuit 31 outputs a generated image signal for display to the monitor 5. Further, the image processing circuit 31 calculates average brightness in an image corresponding to one frame in the image signal which is outputted from the image control circuit 22, and outputs the calculated signal to the light source apparatus 3 as a light adjustment signal, and the light source apparatus 3 adjusts a light amount of illuminating light that is caused to be incident on the light guide 12 from the light source apparatus 3 based on the light adjustment signal.

Note that the image signal which is outputted from the imager control circuit 22 may be also inputted to the control circuit 32, and the control circuit 32 may perform such control as to restrict the condition of performing the first operation mode to the case where an upper limit value of a signal level of the image signal which is inputted is a predetermined threshold value or less by monitoring whether or not the upper limit value of the signal level of the image signal which is inputted is the predetermined threshold value or less.

The light source apparatus 3 includes a lamp 35 configured to generate illuminating light, a lamp control circuit 36 configured to control a light amount of the illuminating light generated by the lamp 35, and a condensing lens 37 configured to condense the illuminating light generated by the lamp 35 and cause the illuminating light to be incident on an end portion to be an incident end of the light guide 12.

Figure 2:
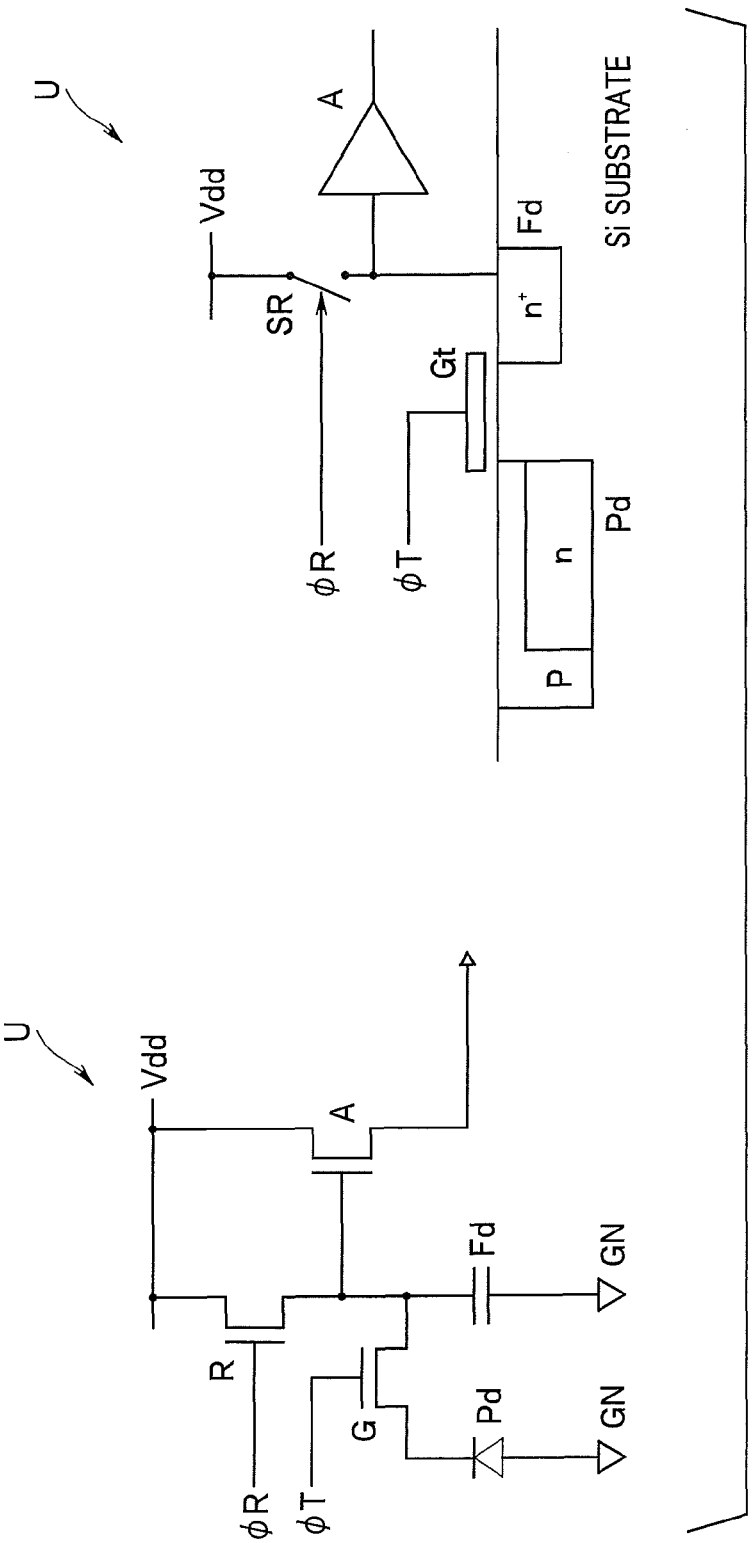
FIG. 2 is a diagram illustrating a configuration example of a unit pixel in a MOS type image pickup device in FIG. 1.

FIG. 2 illustrates a configuration of a unit pixel U of the MOS type image pickup device 16. Note that a right side in FIG. 2 illustrates a semistructured configuration of the unit pixel, and a left side in FIG. 2 illustrates an equivalent circuit configuration of the unit pixel.

As illustrated on the left side, the unit pixel includes a photodiode Pd forming a photoelectric conversion element configured to perform photoelectric conversion in accordance with a light reception amount of incident light, a transferring transistor G forming a transfer section configured to transfer electric charges accumulated in the photodiode Pd to an electric charge conversion section, a capacitor Fd forming the electric charge conversion section configured to convert electric charges into signals, an amplifier A forming a signal output section configured to output a signal of the capacitor Fd, and a resetting transistor R forming a reset section configured to reset the signal of the capacitor Fd. Note that a cathode of the photodiode Pd and one end of the capacitor Fd are connected to a ground GND (abbreviated as GN in FIG. 2 and FIG. 3). Further, a power supply voltage Vdd is applied to drains of transistors forming the resetting transistor R and the amplifier A.

A transfer signal $\varphi T$ is applied to a gate of the transferring transistor G, and resistance between a source and a drain of the transferring transistor G is turned on and off respectively in accordance with "H" and "L" levels of the transfer signal φT.

When the transferring transistor G is turned on, the electric charges accumulated in the photodiode Pd are transferred to the capacitor Fd, and the electric charges accumulated in the capacitor Fd are converted into a signal of a voltage value corresponding to an electric charge amount.

When the transferring transistor G is turned off, electric charges in a state corresponding to a black level accumulated in the capacitor Fd in a state where the electric charges accumulated in the photodiode Pd are not transferred to the capacitor Fd are converted into a signal.

Further, a reset signal φR is applied to a gate of the resetting transistor R, whereby resistance between a drain of the resetting transistor R, and a source to which the capacitor Fd and a gate to be an input end of the amplifier A are connected is turned on respectively, and the signal of the capacitor Fd and an output of the amplifier A are reset.

Note that when a plurality of pixels are adopted, a selecting transistor (refer to FIG. 3) configured to select outputs of the respective amplifiers A (of the unit pixels) is connected to output ends of the respective amplifiers A.

At the right side of FIG. 2, a photodiode Pd at the left side in FIG. 2 is formed by pn-bond on an Si substrate, and a transfer gate electrode Gt forming the transferring transistor G, a high concentration impurity region $n^+$ forming the capacitor Fd, and a resetting switch SR forming the resetting transistor R are illustrated.

Figure 3:
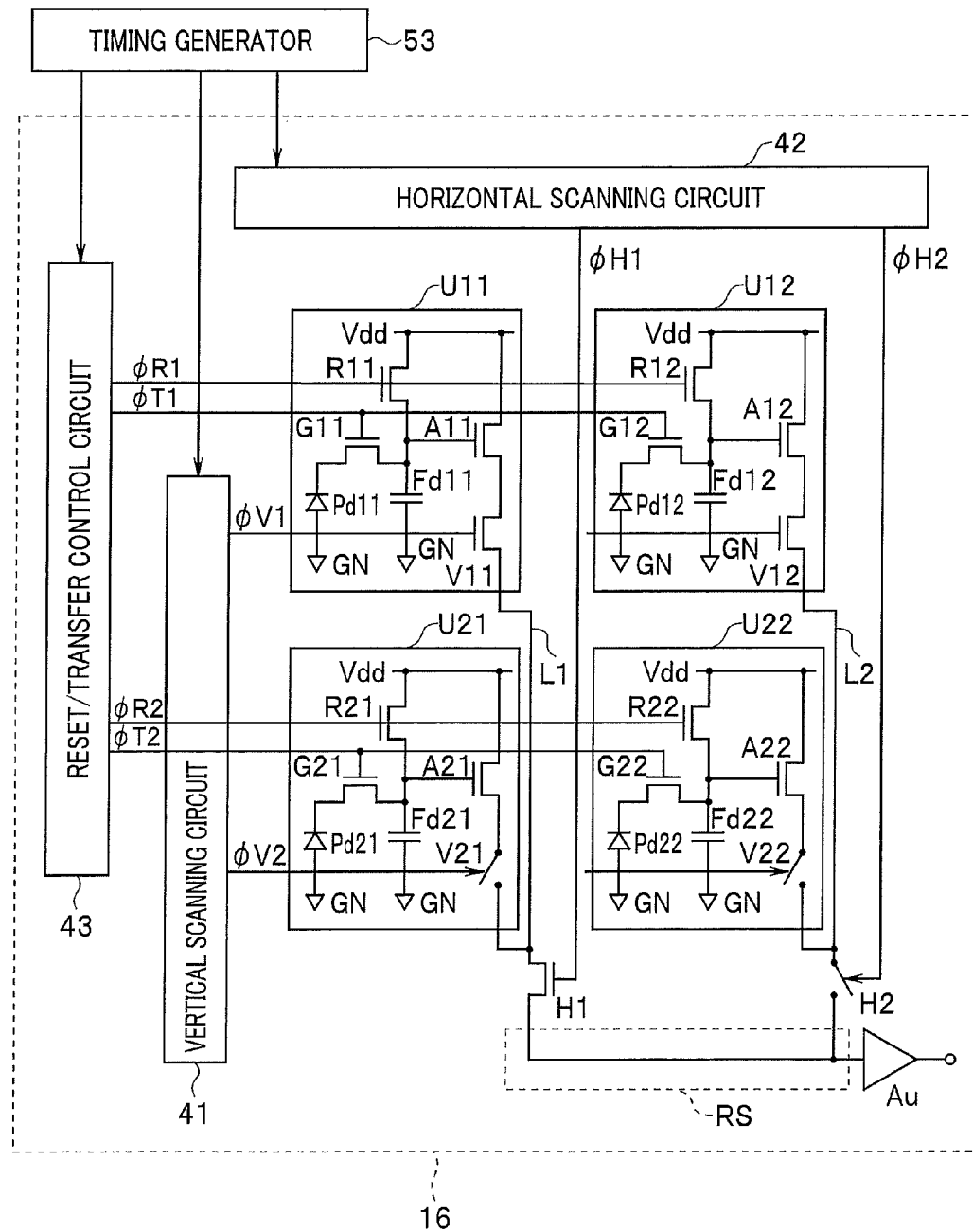
FIG. 3 is a diagram illustrating a circuit configuration of the MOS type image pickup device.

FIG. 3 illustrates a configuration of the MOS type image pickup device 16 in which a plurality of unit pixels U in FIG. 2 are disposed in a lattice shape along a vertical direction and a horizontal direction that are orthogonal to each other. Note that FIG. 3 illustrates an example of pixels U11, U12, U21 and U22 that are disposed in such a manner that two pixels are disposed in each of the vertical direction and the horizontal direction by simplification. Further, in FIG. 3, constituent elements such as the photodiode Pd configuring the unit pixel U in FIG. 2 is illustrated by a photodiode Pdij or the like configuring a pixel Uij (i and j are 1 or 2 in FIG. 3). Note that in the present embodiment, an optical image of the objective lens 15 is formed on all the pixels in FIG. 3, and the MOS type image pickup device 16 in the present embodiment is a MOS type image pickup device that is configured by only effective pixels without including OB pixels.

As illustrated in FIG. 3, at an output end of an amplifier Aij of the pixel Uij, a (vertical column) selecting transistor Vij for outputting an output signal of the amplifier Aij to a vertical transfer line Lj is provided.

Further, the MOS type image pickup device 16 includes a vertical scanning circuit 41 and a horizontal scanning circuit 42 configured to generate a vertical selection signal φVj for selecting a pixel column in the vertical direction in the pixel Uij, and a horizontal selection signal φHi for selecting a pixel row in the horizontal direction respectively, and a reset/transfer control circuit (or a reset/transfer generation circuit) 43 configured to generate a reset signal φRj and a transfer signal φTj.

Further, the MOS type image pickup device 16 is provided with a (horizontal row) selecting transistor Hi for selecting one vertical transfer line in the horizontal direction in a plurality of vertical transfer lines L1 and L2, and an output amplifier Au connected to the selecting transistor Hi, the selecting transistor Hi is selected by the horizontal selection signal φHi that is outputted from the horizontal scanning circuit 42, and a signal of a pixel selected by the horizontal selection signal φHi is outputted from the output amplifier Au. Note that in FIG. 2, a horizontal line that has the selecting transistors H1 and H2 connected, and is connected to an input end of the output amplifier Au may be configured by a shift resistor RS as illustrated by a dotted line.

As will be described later, electric charges that are received by a plurality of photodiodes Pdij in the MOS type image pickup device 16, and are photoelectrically converted are each converted into a signal corresponding to the accumulated electric charges in the capacitor Fdij forming the electric charge conversion section, and signals of the pixels U1j and U2j in the horizontal direction selected by the vertical selection signal φVj are respectively outputted to the vertical transfer lines L1 and L2, and signals of the pixels U1j and U2j in the horizontal direction selected by the horizontal selection signal φH1 and φH2 are respectively outputted from the output amplifier Au.

Further, in the present embodiment, control is performed so that in a state where the transfer section is turned off, signals of the black levels are outputted from the MOS type image pickup device 16, and is subjected to A/D conversion to be stored in the memory 23. In the state where the transfer section is turned on after signal values of the black levels are stored in the memory 23, the acquired signals are outputted from the MOS type image pickup device 16, and the correction circuit 24 generates an image signal in which the black levels are corrected by subtracting the signal values of the black levels stored in the memory 23.

The plurality of photodiodes Pdij in the MOS type image pickup device 16 form the light receiving section 45 (refer to FIG. 4) of the MOS type image pickup device 16, the vertical scanning circuit 41, the horizontal scanning circuit 42 and the reset/transfer control circuit 43 form a reading section 46 (refer to FIG. 4) that reads signals based on light reception by the light receiving section 45 of the MOS type image pickup device 16 from the respective pixels, and the output amplifier Au forms an output section 47 (refer to FIG. 4) that outputs the signals by the MOS type image pickup device 16.

Operations of the vertical scanning circuit 41, the horizontal scanning circuit 42 and the reset/transfer control circuit 43 which form the above described reading section 46 are controlled by a timing generator 53 that configures the image pickup device control circuit 17. Further, the image pickup device control circuit 17 controls an operation of the MOS type image pickup device 16 based on an operation mode control signal MODE and the like that is transmitted from the control circuit 32.

Note that FIG. 3 illustrates a state where the vertical selection signal φV1 is turned on (the vertical selection signal φV2 is turned off), and the horizontal selection signal φH1 is turned on (the horizontal selection signal φH2 is turned off), whereby the signal of the pixel U11 is outputted from the output amplifier Au.

Figure 4:
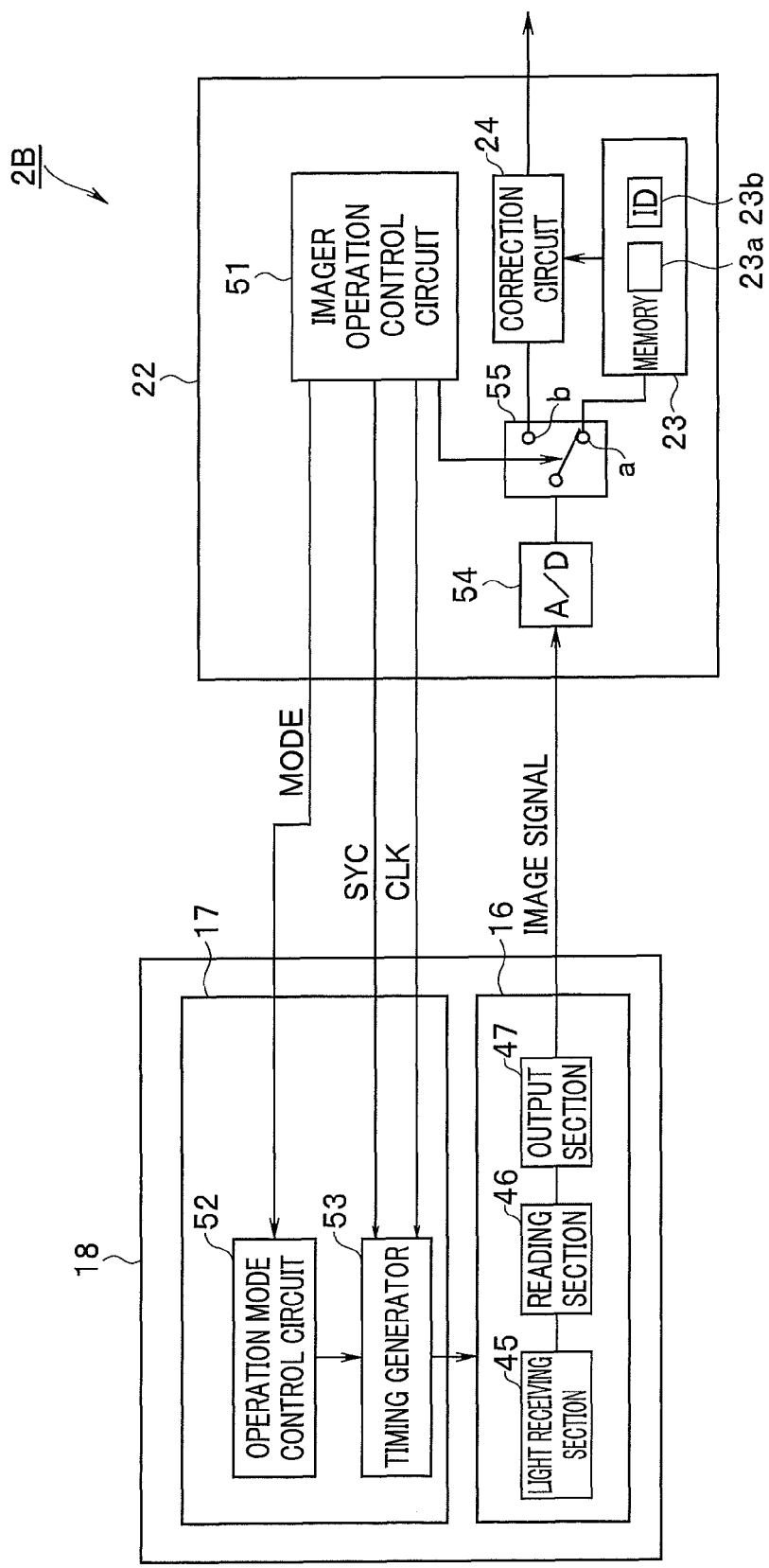
FIG. 4 is a diagram illustrating configurations of an imager and an imager control circuit.
Figure 5:
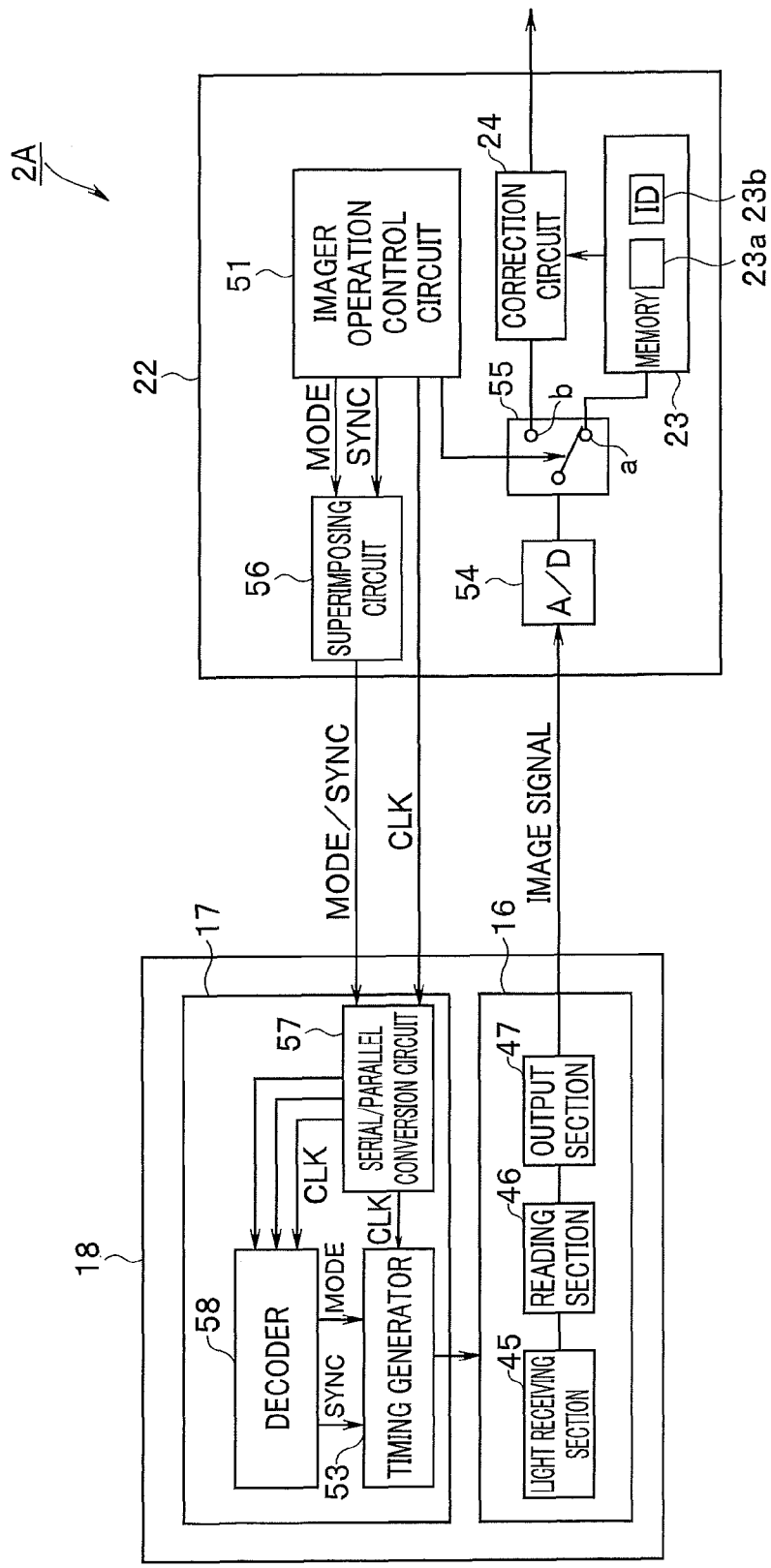
FIG. 5 is a diagram illustrating configurations of the imager and the imager control circuit in a case where a number of signal lines in FIG. 4 is reduced.

FIG. 4 illustrates configurations of the imager 18 in the case of the endoscope 2B, and the imager control circuit 22, whereas FIG. 5 illustrates configurations of the imager 18 in the case of the endoscope 2A, and the imager control circuit 22.

In the endoscope 2B, the imager 18 and the imager control circuit 22 are connected by four of the signal lines 19 which are inserted through the inside of the insertion portion 6, as illustrated in FIG. 4. In the endoscope 2A, the imager 18 and the imager control circuit 22 are connected by three of the signal lines 19 which are inserted through the inside of the insertion portion 6, as illustrated in FIG. 5. Note that in addition to the above, two of the signal lines 19 which respectively transmit the power supply voltage Vdd and the ground GND potential are inserted through the inside of the insertion portion 6 (not illustrated in FIG. 4 and FIG. 5).

In the endoscope 2B in FIG. 4, an imager operation control circuit 51 in the imager control circuit 22 transmits the operation mode control signal (or the mode control signal) MODE that controls the operation mode, a synchronous signal SYNC, and a clock signal CLK respectively to the image pickup device control circuit 17 via the single signal line 19. Further, the image signal which is outputted from the MOS type image pickup device 16 of the imager 18 is transmitted to the imager operation control circuit 51 via the signal line 19.

The operation mode control signal MODE which is transmitted from the imager operation control circuit 51, the synchronous signal SYNC and the clock signal CLK include an operation mode control circuit 52 configuring the image pickup device control circuit 17 and configured to control the operation mode, and a timing generator 53 configured to generate a timing signal that controls the MOS type image pickup device 16.

The timing generator 53 (under control of the control circuit 32) controls the vertical scanning circuit 41, the horizontal scanning circuit 42 and the reset/transfer control circuit 43 that form the reading section 46 as illustrated in FIG. 3 (also can be defined to control the light receiving section 45 and the reading section 46. Further, when a horizontal shift register is provided at a pre-stage of the output amplifier Au in FIG. 3, the timing generator 53 also controls the output section 47).

Further, the imager control circuit 22 includes the imager operation control circuit 51 configured to control the operation of the imager 18 under control of the control circuit 32, an A/D conversion circuit 54 configured to convert an (analogue) image signal (or a pixel signal) that is outputted from the MOS type image pickup device 16 into a digital image signal, a changeover switch 55 configured to switch an output signal of the A/D conversion circuit 54, the memory 23 configured to store signal values of an image signal of black levels in a case of a contact point a of the changeover switch 55 being selected, and the correction circuit 24 configured to perform correction of an image signal in a case of a contact point b of the changeover switch 55 being selected. Instead of the A/D conversion circuit 54 illustrated in FIG. 4, an analogue front end (AFE) and a correlated double sampling circuit (CDS) or the like may be used.

Note that the imager operation control circuit 51 controls the changeover switch 55 based on the operation mode control signal MODE. More specifically, the imager operation control circuit 51 switches the changeover switch 55 so as to select the contact point a in an operation period of the first operation mode, and select the contact point b in an operation period of the second operation mode. In the memory 23, the aforementioned signal value storage section 23a and the ID storage section 23b in which ID is stored are formed respectively by some storage regions different from each other.

In contrast with this, in the endoscope 2A in FIG. 5, the imager operation control circuit 51 in the imager control circuit 22 transmits the operation mode control signal MODE that controls the operation mode and the synchronous signal SYNC by superimposing the operation mode control signal MODE and the synchronous signal SYNC on each other to the image pickup device control circuit 17 via the single signal line 19. The other signal lines 19 are the same as in the case of FIG. 4.

In the endoscope 2A in FIG. 5, the imager control circuit 22 has a configuration further including a superimposing circuit (or an encoder) 56 configured to superimpose (or encode) the operation mode control signal MODE and the synchronous signal SYNC in the imager control circuit 22 in FIG. 4.

Further, in the endoscope 2A in FIG. 5, a serial/parallel conversion circuit 57 configured to perform serial/parallel conversion, and a decoder 58 configured to decode the operation mode control signal MODE and the synchronous signal SYNC which are encoded, instead of the operation mode control circuit 52 in the image pickup device control circuit 17 in FIG. 4.

Figure 6:
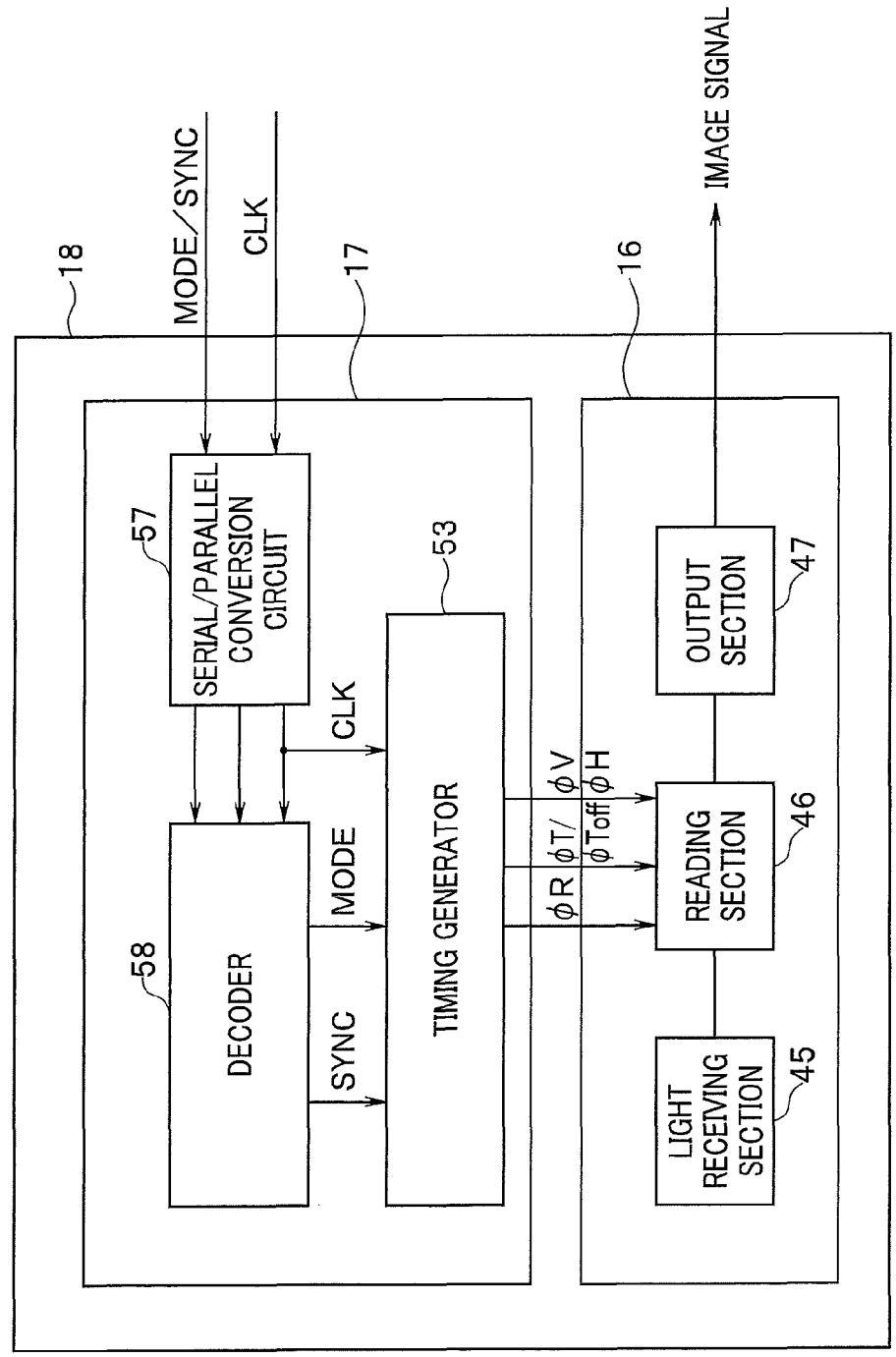
FIG. 6 is a diagram illustrating the configuration of the imager in FIG. 5.

FIG. 6 illustrates a configuration of the imager 18 in the case of FIG. 5. Note that when the timing generator 53 causes the MOS type image pickup device 16 to operate by switching the first operation mode and the second operation mode, an operation of driving the MOS type image pickup device 16 without outputting the transfer signal φT, and an operation of driving the MOS type image pickup device 16 by outputting the transfer signal φT make a decisive difference, as will be described in FIG. 7 to FIG. 9B.

In other words, the timing generator 53 conducts control so as to output the reset signal φR, the vertical selection signal φV and the horizontal selection signal φH to the reading section 46 without outputting the transfer signal φT (schematically illustrated by φToff in FIG. 6) in the first operation mode, and output the transfer signal φT, the reset signal φR, the vertical selection signal φV and the horizontal selection signal φH to the reading section 46 in the second operation mode.

In the case of the configuration in FIG. 4, a control content of the timing generator 53 is the same as in the case illustrated in FIG. 6.

The image pickup apparatus 1 of the present embodiment includes the MOS type image pickup device 16 configured to form the solid state image pickup device including a plurality of pixels with the photodiode Pd (or Pdij) forming the photoelectric conversion element configured to perform photoelectric conversion corresponding to a light reception amount, and accumulate electric charges, the transferring transistor G (or Gij) forming the transfer section configured to transfer the electric charges accumulated in the photoelectric conversion element, the capacitor Fd (or Fdij) forming the electric charge conversion section configured to convert the transferred electric charges into a signal, the resetting transistor R (or Rij) forming the reset section configured to reset the signal of the charge conversion section, the amplifier A (or Aij) forming the signal output section configured to output the signal converted by the electric charge conversion section, and the vertical transfer line L (or L1 and L2) connected to the signal output section, as the unit pixel, and the image signal processing apparatus 4 and the imager control circuit 22 that form the signal processing apparatus including the setting section 33a configured to set operation timings of the first operation mode of outputting a pixel signal of a black level as a result of making a signal level of the electric charge conversion section the black level by bringing the reset section into an off state, and bringing the transfer section into an off state, and the second operation mode of outputting the signal of the charge conversion section to the vertical transfer line L via the signal output section, as an ordinary pixel signal in which a black level is not corrected, after transferring the electric charges accumulated by the photoelectric conversion element to the electric charge conversion section by bringing the reset section into an off state from an on state, and bringing the transfer section into an on state, the control circuit 32 (or the image pickup device control circuit 17) forming the operation mode control section configured to switch the first operation mode and the second operation mode in accordance with setting of the setting section 33a, and the correction circuit 24 forming the black level correction section configured to correct the black levels in the image signal formed of the ordinary pixel signal in plurality which are outputted from the output amplifier Au forming the output section of the solid state image pickup device in the second operation mode, the signal processing apparatus holds the pixel signal values of the black levels acquired in the first operation mode in the operation timing set by the setting section 33a, in the memory 23, and the black level correction section corrects the image signal acquired in the second operation mode by using the pixel signal values of the black levels held in the memory 23.

Figure 7:
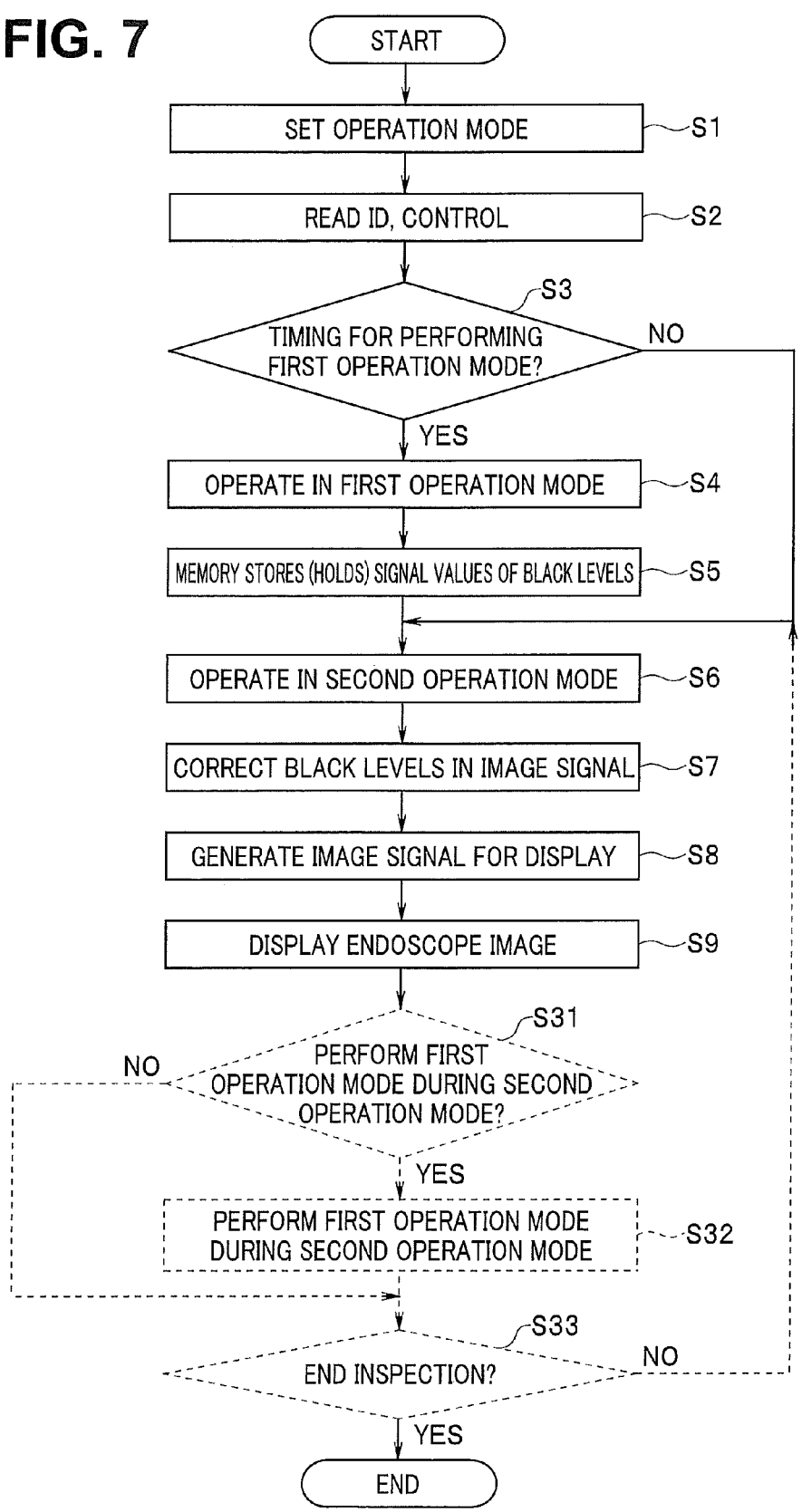
FIG. 7 is a flowchart illustrating an entire processing content of the first embodiment.

Next, an operation of the image pickup apparatus 1 of the present embodiment will be described with reference to FIG. 7. FIG. 7 illustrates a flowchart showing an entire processing content of the image pickup apparatus 1.

A user such as a surgeon turns on the power supply of the image pickup apparatus 1 in which the endoscope 2A or 2B is connected to the image signal processing apparatus 4, and brings the image pickup apparatus 1 into an operation state.

In first step S1, the user sets timing or the like for operating the two operation modes, or the first operation mode from the setting section 33a of the operation panel 33. The operation modes have a configuration in which only one operation mode in the two operation modes can be executed, and therefore, when the first operation is set, setting of the second operation mode (in an operation period in which the first operation mode is not set) is automatically determined. In the memory 32a in the control circuit 32, information is stored, that the timing is set so that operation is performed in the first operation mode at an actuation time, in a case of default setting.

Note that when the MOS type image pickup device is operated as described above, the MOS type image pickup device can be operated in only one of the operation modes (cannot be operated in the two operation modes simultaneously, in other words), but it becomes possible to operate the MOS type image pickup device so as to read pixels of a plurality of lines in the second operation mode, (switch the operation mode from the second operation mode to the second operation mode) during the second operation mode, and read pixels of one line in the first operation mode, for example, as will be described later.

The user may operate the image pickup apparatus 1 with the default setting, or besides the default setting, setting can be made by the setting section 33a so as to cause the image pickup apparatus 1 to operate by the first operation mode during endoscope inspection.

Note that in the signal value storage section 23a of the memory 23, the pixel signal value of the black level to be a reference is stored in advance at a time of factory shipment of the endoscope 2K. Consequently, even when the MOS type image pickup device 16 is caused to operate in the second operation mode without performing the first operation mode, correction of the black level of the image signal in the second operation mode can be performed by using the pixel signal value of the black level of the reference.

In next step S2 after setting of the first operation mode is performed, the control circuit 32 reads the ID of the memory 23, and performs control corresponding to the ID. The control circuit 32 judges whether the endoscope connected to the image signal processing apparatus 4 is 2A or 2B from the read ID, for example, and can perform control corresponding to a kind of the endoscope 2K which is judged.

In next step S3, the control circuit 32 judges whether or not it is timing for causing the MOS type image pickup device 16 to operate in the first operation mode based on the information or the like stored in the memory 32a, in order to cause the MOS type image pickup device 16 to operate.

In a case of the setting of performing the first operation mode at the time of actuation, in next step S4, the control circuit 32 controls the imager control circuit 22 to cause the MOS type image pickup device 16 to operate in the first operation mode. Note that setting of performing the first operation mode simultaneously at the time of adjustment of white balance that is usually performed at the time of actuation may be made. In that case, the MOS type image pickup device 16 of the imager 18 operates in the first operation mode. Processing in the case of the first operation mode is as in FIG. 8A (to be described later).

The pixel signals (also referred to as a first image signal) corresponding to the black levels of the respective pixels outputted from the MOS type image pickup device 16 in the first operation mode are inputted to the imager control circuit 22 as illustrated in FIG. 4 or FIG. 5. In this case, the changeover switch 55 is switched so that the contact point a is turned on, and the pixel signals of the black levels inputted to the imager control circuit 22 are subjected to A/D conversion, and thereafter, are inputted to the memory 23 through the changeover switch 55. Subsequently, as illustrated in step S5, the signal values of the black levels are stored in the signal value storage section 23a of the memory 23.

Note that the signal value storage section 23a of the memory 23 includes a second signal value storage region configured to store the signal values of the black levels acquired when the first operation mode is set so as to be able to use the second signal value storage region selectively, for example, in addition to the region for storing the signal value of the black level (of default) at the time of factory shipment.

Consequently, the user can select the case of performing correction of the black levels by using the signal value of the black level of default, and the case of performing correction of the black levels by using the signal values of the black levels acquired in the case of the first operation mode being set. When the user sets to perform the first operation mode, correction of the black levels is performed by using the signal values of the black levels acquired in the first operation mode (automatically). Note that when the black levels are acquired at the time of maintenance, the signal value of the black level of default may be updated based on the signal values of the black levels which are acquired. By doing so, default setting (or update) effectively corresponding to a characteristic change can be made at the time of maintenance, with respect to the case in which characteristics of the black levels of the MOS type image pickup device 16 change over time.

When the processing of storing the signal values of the black levels in all the pixels (a plurality of pixels corresponding to one frame, in other words) forming the light receiving section 45 of the MOS type image pickup device 16 in the memory 23 is ended, the control circuit 32 controls the imager control circuit 22 to cause the MOS type image pickup device 16 of the imager 18 to operate in the second operation mode in next step S6. Subsequently, the MOS type image pickup device 16 operates in the second operation mode. Processing in this case is as in FIG. 9A (to be described later).

In a case of a judgment result that it is not the operation timing for the first operation mode in the judgment processing in step S3, the flow goes to the processing in step S6.

The second image signal which is outputted from the MOS type image pickup device 16 which operates in the second operation mode in step S6 is subjected to A/D conversion in the imager control circuit 22, and thereafter is inputted to the correction circuit 24. Subsequently, in step S7, the correction circuit 24 subtracts the signal values of the black levels in the memory 23 from the second image signal which is inputted, and outputs the image signal with the black levels corrected.

The image signal is inputted to the image processing circuit 31, and in step S8, the image processing circuit 31 performs outline correction, γ correction and the like, generates the image signal for display and outputs the image signal for display to the monitor 5. As shown in step S9, the monitor 5 receives the image signal for display, and thereby displays the corresponding image as the endoscopic image, whereby the processing in FIG. 7 is ended. Note that as illustrated by dotted lines in FIG. 7, processing in steps S31 to S33 may be performed after the processing in step S9 (to be described later).

Next, with reference to FIG. 8A and FIG. 8B, processing in the case of the first operation mode will be described. Note that processing in step S16 in FIG. 8A shows substantially the same processing as in step S5 in FIG. 7.

When the first operation mode starts, the timing generator 53 of the image pickup device control circuit 17 performs control so that the reset/transfer control circuit 43 outputs the reset signal φR in step S11.

Figure 8A:
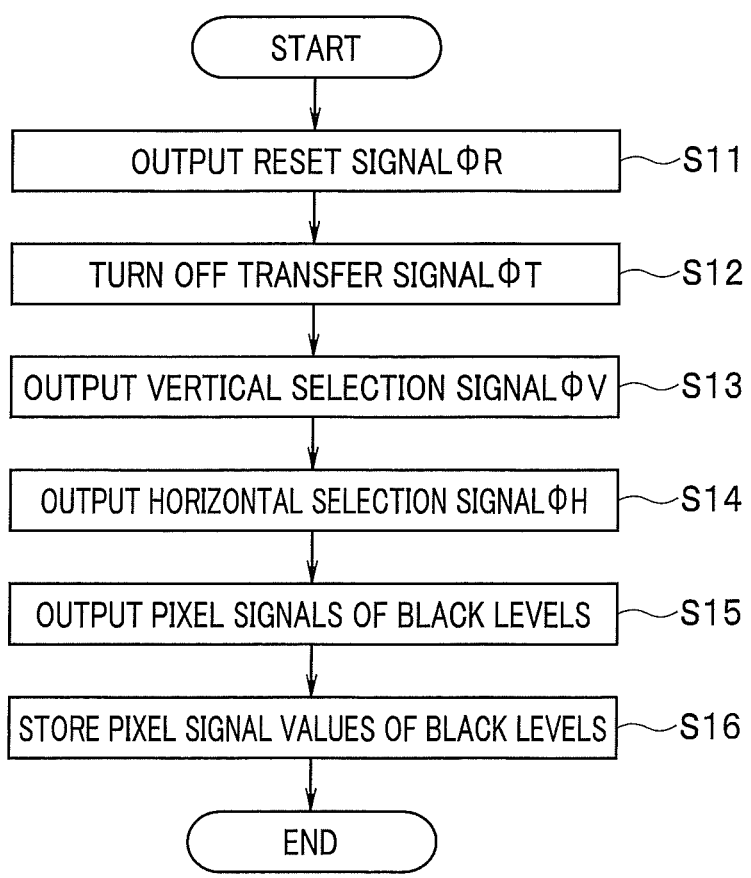
FIG. 8A is a flowchart illustrating a processing content of a first operation mode that generates a pixel signal value of a black level.
Figure 8B:
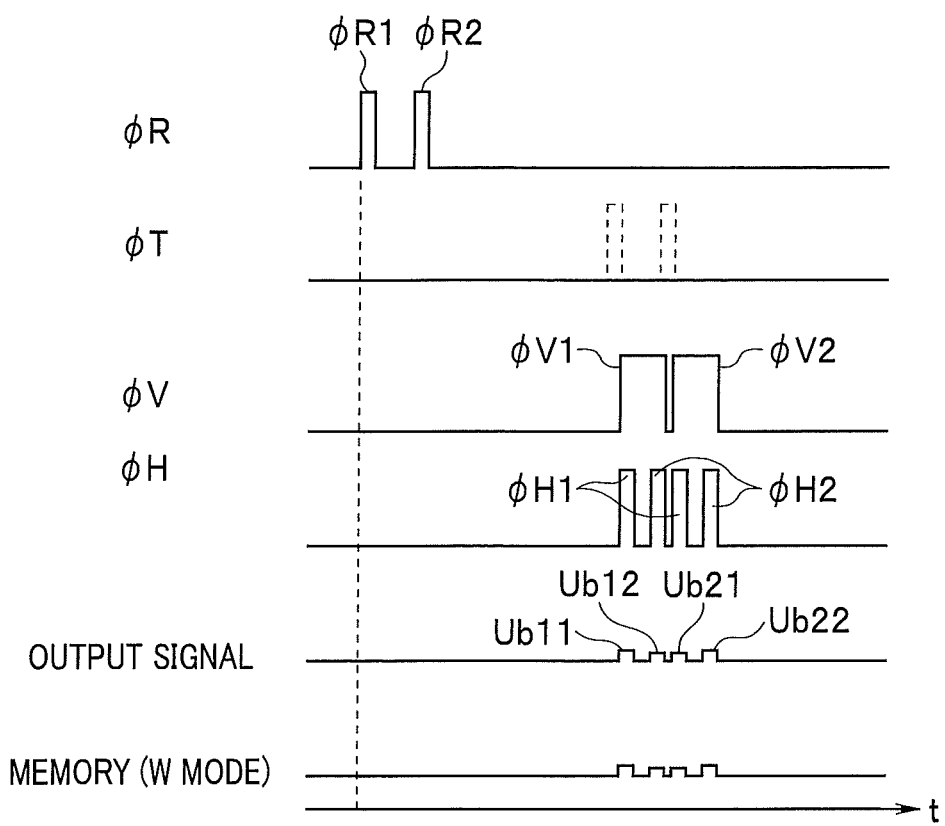
FIG. 8B is a timing chart of operation explanation of the first operation mode.

FIG. 8B illustrates a timing chart (corresponding to the case of the configuration in FIG. 3) corresponding to the processing in FIG. 8A.

The reset/transfer control circuit 43 sequentially outputs φR1 and φR2 as the reset signal φR. In the case of the configuration of FIG. 3, by the reset signal φR1, the resetting transistors R11 and R12 in the pixels U11 and U12 are turned on, and outputs of the capacitors Fd11 and Fd12 and the amplifiers A11 and A12 are reset. Similarly, by the reset signal φR2, the resetting transistors R21 and R22 of the pixels U21 and U22 are turned on, and the outputs of the capacitors Fd21 and Fd22 and the amplifiers A21 and A22 are reset.

Further, in step S12, the timing generator 53 performs control so that the reset/transfer control circuit 43 does not output the transfer signal φT, and the transferring transistor G is turned off (the state of off is kept). In FIG. 8B, the dotted lines indicate that the transfer signal φT is not outputted.

In next step S13, the timing generator 53 performs control so that the vertical scanning circuit 41 outputs the vertical selection signal φV. FIG. 8B illustrates a state in which the vertical scanning circuit 41 outputs the vertical selection signals φV1 and φV2 at a timing when a predetermined time period elapses after the vertical scanning circuit 41 sequentially outputs the reset signals φR1 and θR2.

In the case of the configuration in FIG. 3, by the vertical selection signal φV1, the signal of the amplifier A11 corresponding to the state of the black level of the pixel U11 is outputted to the vertical transfer line L1, and the signal of the amplifier A12 is outputted to the vertical transfer line L2. Similarly, by the vertical selection signal φV2, the signal of the amplifier A21 corresponding to the state of the black level of the pixel U21 is outputted to the vertical transfer line L1, and the signal of the amplifier A22 is outputted to the vertical transfer line L2.

In next step S14, the timing generator 53 performs control so that the horizontal scanning circuit 42 outputs the horizontal selection signal φH within a period in which the vertical selection signals φV1 and φV2 are respectively outputted. FIG. 8B illustrates a state where the horizontal scanning circuit 42 sequentially outputs the horizontal selection signals φH1 and φH2 in a period in which the vertical selection signal φV1 is outputted, and sequentially outputs the horizontal selection signals φH1 and φH2 within a period in which the vertical selection signal φV2 is outputted.

By the processing in step S14, the pixel signals corresponding to the black levels of the respective pixels Uij are sequentially outputted from the MOS type image pickup device 16 through the output amplifier Au as shown in step S15. In FIG. 8B, the pixel signals Ub11, Ub12, Ub21 and Ub22 of the black levels (in the pixels U11, U12, U21 and U22) are outputted from the output amplifier Au as the output signals (of the MOS type image pickup device 16).

In this case, the memory 23 is set at a write mode (illustrated as a W mode in FIG. 8B), and as shown in step S16, the pixel signals Ub11, Ub12, Ub21 and Ub22 of the black levels are subjected to A/D conversion, and the digital pixel signal values of the black levels are related to addresses of the respective pixels Uij and are stored in the memory 23.

In this way, the processing of the first operation mode is ended.

Next, with reference to FIG. 9A and FIG. 9B, processing in a case of the second operation mode will be described.

In the second operation mode which will be described hereunder, the processing of not outputting the transfer signal φT in the processing in the first operation mode in FIG. 8A is changed to processing of outputting the transfer signal φT, and other processing is the processing which is performed as in the first operation mode. However, processing to the output signal outputted from the MOS type image pickup device 16 differs from the case of the processing in the first operation mode. Note that step S26 in FIG. 9A shows processing substantially similar to the processing in step S7 in FIG. 7.

When the second operation mode is started, in step S21, the timing generator 53 of the image pickup device control circuit 17 performs control so that the reset/transfer control circuit 43 outputs the reset signal φR.

Figure 9A:
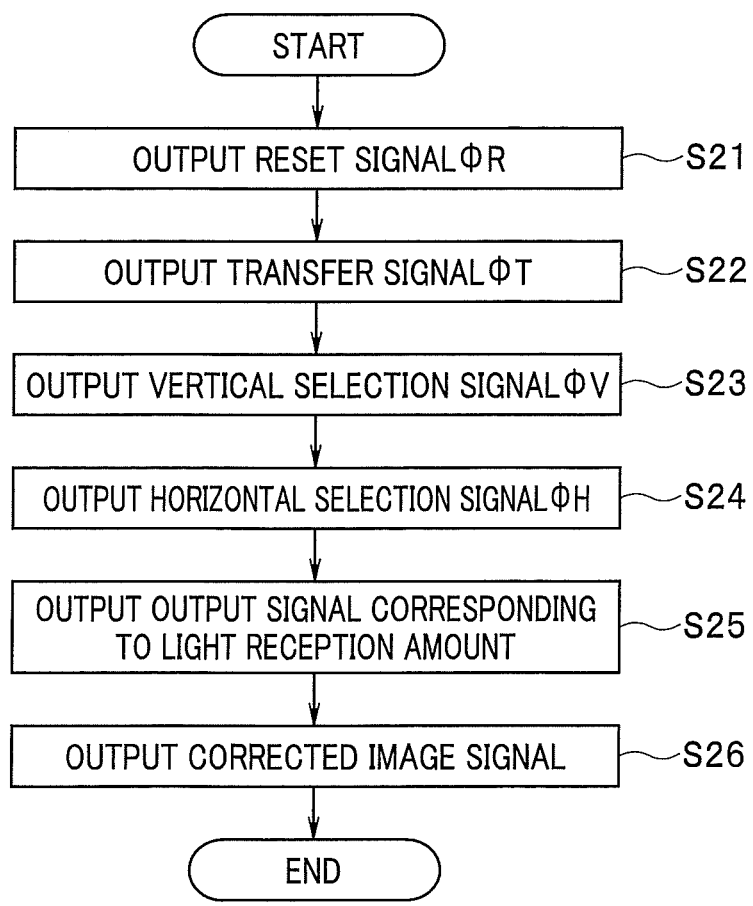
FIG. 9A is a flowchart illustrating a processing content of a second operation mode that is a normal mode.
Figure 9B:
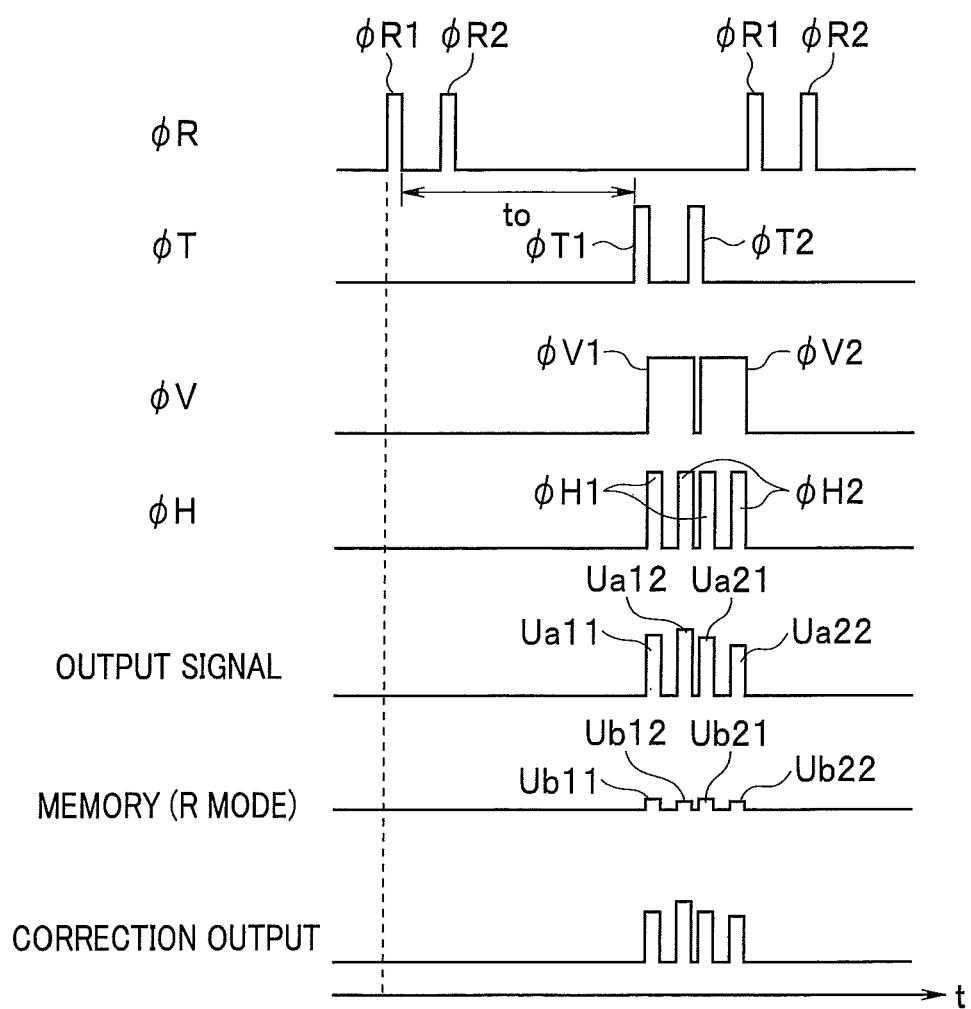
FIG. 9B is a timing chart of operation explanation of the second operation mode.

FIG. 9B illustrates a timing chart (corresponding to the case of the configuration in FIG. 3) corresponding to the processing in FIG. 9A. The reset/transfer control circuit 43 sequentially outputs φR1 and φR2 as the reset signal φR similarly to what is illustrated in FIG. 8B. In the case of the configuration of FIG. 3, by the reset signal φR1, the resetting transistors R11 and R12 in the pixels U11 and U12 are turned on, and outputs of the capacitors Fd11 and Fd12 and the amplifiers A11 and A12 are reset.

Similarly, by the reset signal φR2, the resetting transistors R21 and R22 in the pixels U21 and U22 are turned on, and the outputs of the capacitors Fd21 and Fd22 and the amplifiers A21 and A22 are reset.

Further, in next step S22, the timing generator 53 performs control so that the reset/transfer control circuit 43 outputs the transfer signal φT, and the transferring transistor G is turned on by the transfer signal φT. In FIG. 9B, after a predetermined time period to after the reset signal φR1 is outputted, the transfer signal φT1 is outputted, and after the predetermined time period to after the reset signal φR2 is outputted, the transfer signal φT2 is outputted. The predetermined time period to corresponds to a light receiving period for the respective pixels to pick up an image corresponding to one frame.

In the case of the configuration in FIG. 3, the electric charges accumulated in accordance with the amount of light received in a predetermined light receiving time period by the photodiodes Pd11 and Pd12 are transferred to the capacitors Fd11 and Fd12 by the transfer signal φT1, and are converted into voltage signals. Further, the electric charges accumulated in accordance with the amount of light received in a predetermined light receiving period by the photodiodes Pd21 and Pd22 are transferred to the capacitors Fd2 and Fd22 by the transfer signal φT2, and are converted into voltage signals.

In next step S23, the timing generator 53 performs control so that the vertical scanning circuit 41 outputs the vertical selection signal φV.

As illustrated in FIG. 9B, the vertical scanning circuit 41 sequentially outputs the vertical selection signal φV1 immediately after the transfer signal φT1, and the vertical selection signal φV2 immediately after the transfer signal φT2.

In the case of the configuration in FIG. 3, by the vertical selection signal φV1, the voltage signals converted in the capacitors Fd11 and Fd12 of the pixels U11 and U12 are amplified by the amplifiers A11 and A12 and are respectively outputted to the vertical transfer line L1. Similarly, by the vertical selection signal φV2, the voltage signals converted in the capacitors Fd21 and Fd22 of the pixels U21 and U22 are amplified by the amplifiers A21 and A22 and are outputted to the vertical transfer line L2.

In next step S24, the timing generator 53 performs control so that the horizontal scanning circuit 42 outputs the horizontal selection signal φH within a period in which the vertical selection signals φV1 and φV2 are sequentially outputted. FIG. 9B illustrates a state where the horizontal scanning circuit 42 outputs the horizontal selection signals φH1 and φH2 within a period in which the vertical selection signal φV1 is outputted, and outputs the horizontal selection signals φH1 and φH2 within a period in which the vertical selection signal φV2 is outputted.

By the processing in step S24, the pixel signals of voltages corresponding to the light reception amounts of the respective pixels Uij are outputted from the MOS type image pickup device 16 through the output amplifier Au as shown in step S25. In FIG. 9B, pixel signals Ua11, Ua12, Ua21 and Ua22 of the voltages corresponding to the light reception amounts (in the pixels U11, U12, U21 and U22) are outputted from the output amplifier Au as the output signals (of the MOS type image pickup device 16). The output signals outputted from the output amplifier Au are inputted to the correction circuit 24.

In this case, the memory 23 is set at a read mode (illustrated as an R mode in FIG. 9B), and (signal values of) the pixel signals Ub11, Ub12, Ub21 and Ub22 of the black levels are read from the memory 23, and are inputted to the correction circuit 24.

Subsequently, as shown in step S26, the correction circuit 24 outputs a pixel signal array in which (the signal values) of the pixel signals Ubij of the black levels are subtracted from the pixel signals Uaij to the image processing circuit 31 at the post stage side as a corrected image signal.

In this way, the processing of the second operation mode illustrated in FIG. 9A is ended.

According to the first embodiment operated like this, the black levels can be corrected easily with high precision even in the case of using an ordinary image pickup device having only one signal read system.

Further, in the first embodiment, the memory 23 holds (stores) the signal values of the black levels of all of a plurality of photoelectric conversion elements, which are outputted from the MOS type image pickup device 16 in the first operation mode, and the correction circuit 24 that forms the black level correction section corrects all of the ordinary pixel signals configuring the image signal which is acquired in the second operation mode respectively according to the signal values of the black levels held in the memory 23, so that black level correction with high precision can be made for each of the respective pixels.

Further, according to the image pickup apparatus 1 adopting the endoscope 2A in the first embodiment, the configuration is adopted, which can transmit the operation mode control signal MODE and the synchronous signal SYNC by using the common signal line 19, so that the insertion portion 6 can be reduced in diameter.

Next, a modification of the first embodiment will be described. In the first embodiment, the case of being able to configure the image pickup apparatus 1 by using the endoscope 2A or 2B is described. In contrast with this, in the modification of the first embodiment, the image pickup apparatus 1 is enabled to be configured by selectively using one of the endoscopes 2A, 2B and 2C. Note that in the present modification, the case of using the endoscope 2A or 2B is the same as the first embodiment, and therefore description (explanation) of the case will be omitted.

Figure 10:
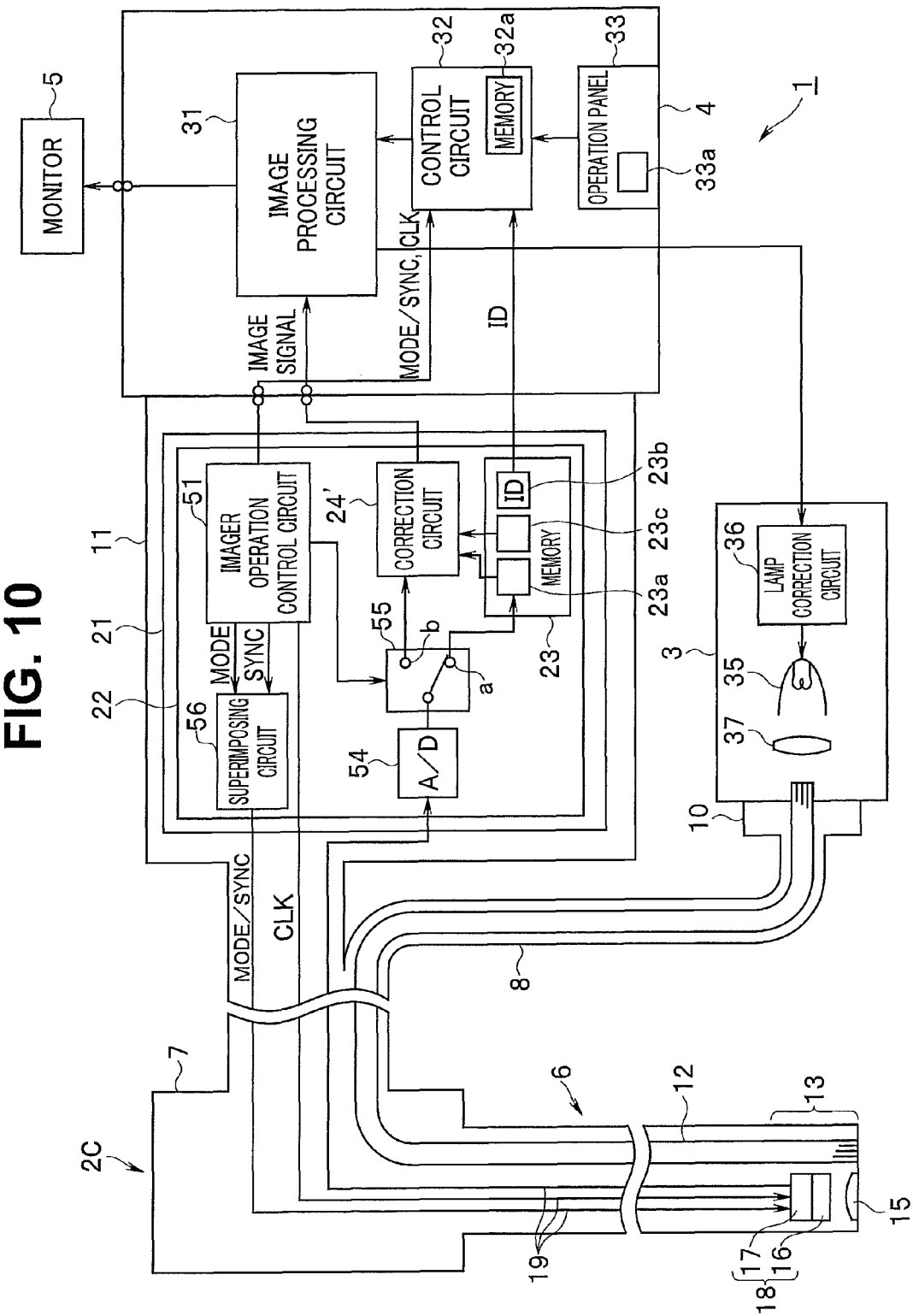
FIG. 10 is a diagram illustrating an entire configuration of an image pickup apparatus of a modification of the first embodiment.

FIG. 10 illustrates the image pickup apparatus 1 in a case of using an endoscope 2C. The image pickup apparatus 1 in FIG. 10 is configured by including the endoscope 2C, the light source apparatus 3, the image signal processing apparatus 4 and the monitor 5, but the endoscope 2A or 2B illustrated in FIG. 1 can be connected to the image signal processing apparatus 4.

The endoscope 2C has a configuration including a correction circuit 24' in which a function of correcting a pixel defect is further added in the configuration of the imager control circuit 22 of the endoscope 2A, for example.

Further, the endoscope 2C further includes a defective pixel address storage section 23c in which information on an address indicating a two-dimensional position of the defective pixel in the MOS type image pickup device 16 is stored in some storage areas in the memory 23, in the memory 23 in the imager control circuit 22 of the endoscope 2A.

As for the endoscope 2C, at a time of factory shipment, for example, the address indicating the two-dimensional position of a defective pixel in the MOS type image pickup device 16 which is mounted on the endoscope 2C is investigated, and information on the address of the defective pixel is stored in the defective pixel address storage section 23c in the memory 23 provided in the same endoscope 2C which is investigated, as a result of the investigation.

Accordingly, the memory 23 of the endoscope 2C includes the signal value storage section 23a that stores the pixel signal values of the black levels, the ID storage section 23b and the defective pixel address storage section 23c. Note that the defective pixel address storage section 23c may be formed by using a memory separate from the memory 23.

Figure 11:
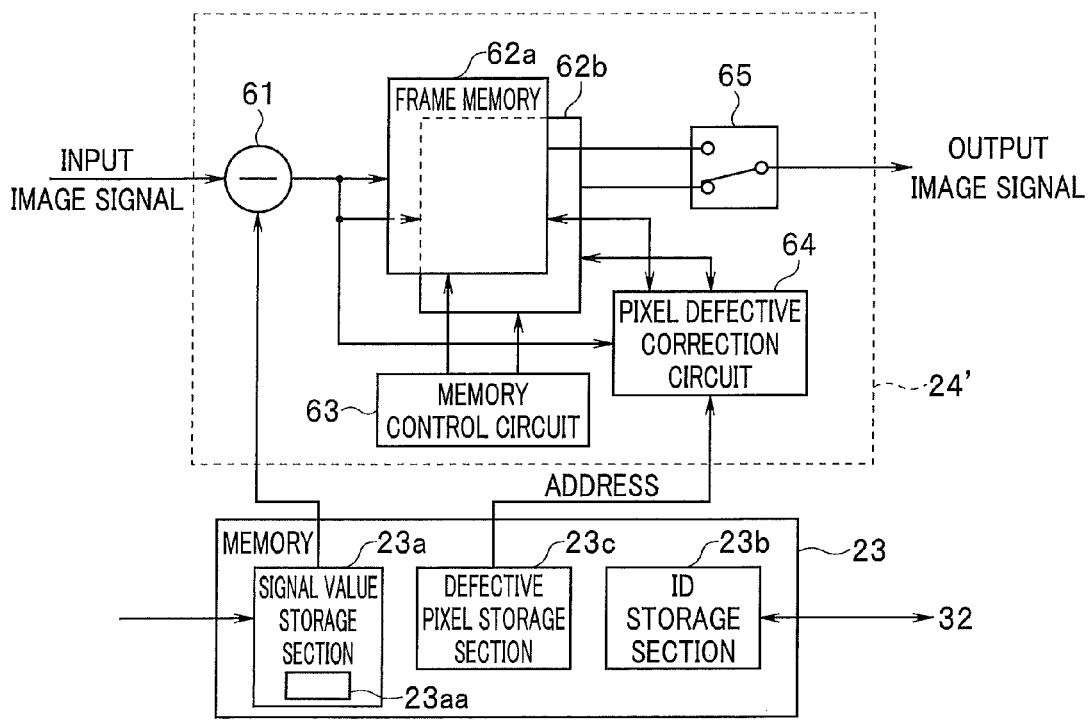
FIG. 11 is a diagram illustrating a configuration example of a correction circuit.

In the present modification, the correction circuit 24' performs correction to a defective pixel as well as correction of black levels to an image signal that is inputted to the correction circuit 24' in the second operation mode, by a configuration as illustrated in FIG. 11, for example.

The correction circuit 24' includes a subtraction circuit 61 configured to output an image signal that is inputted in the second operation mode, and an image signal in which black levels are corrected by subtracting the signal values of the black levels read from the black level (signal value) storage section 23b of the memory 23, two frame memories 62a and 62b each configured to store one frame of the image signal outputted from the subtraction circuit 61, a memory control circuit 63 configured to control write and read of the frame memories 62a and 62b, a defective pixel correction circuit 64 configured to correct a defective pixel in the image signal temporarily stored in the frame memories 62a and 62b and store the image signal in the frame memories 62a and 62b, and a switch circuit 65 configured to switch and output the image signal that is stored in the frame memories 62a and 62b and has the defective pixel corrected.

The memory control circuit 63 alternately writes the image signal which is inputted in the two frame memories 62a and 62b by switching the image signal at each frame, for example. Further, the defective pixel correction circuit 64 performs correction by using signal values of a plurality of pixels around a defective pixel to (an image signal of) a pixel of an address of the defective pixel transmitted from the defective pixel address storage section 23c, to the image signal which is inputted to one of the frame memories to which write of the inputted image signal is performed.

Figure 12:
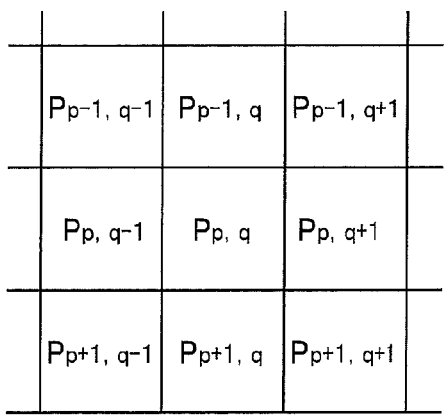
FIG. 12 is a diagram illustrating a defective pixel and pixels around the defective pixel.

In the case of performing correction of (the image signal of) a defective pixel, surrounding pixels adjacent to the defective pixel are used as illustrated in FIG. 12, for example.

When a defective pixel of an address (p,q) is expressed by Pp, q as illustrated in FIG. 12, for example, the defective pixel correction circuit 64 corrects the defective pixel Pp, q by using an average value of signal values of pixels Pp−1, q and Pp+1, q adjacent in a vertical direction, for example, and the corrected signal value is stored in the address of the defective pixel in the frame memory. In this way, the defective pixels in the respective frames are corrected, and at a time of a next frame, the image signal in which the black levels and the defective pixel are corrected is outputted from the correction circuit 24' through the switch circuit 65 from the frame memory in which the image signal in which the defective pixel is corrected is stored. Note that the case of correcting the defective pixel Pp, q is not limited to the case of using the two pixels Pp−1, q and Pp+1, q that are adjacent in the vertical direction, but the defective pixel may be corrected by using two pixels adjacent in the horizontal direction, or eight pixels around the defective pixel Pp, q. Note that as the correction circuit 24 that does not perform correction of a defective pixel but performs correction of black levels, a configuration in which the pixel defective correction circuit 64 is deleted in the configuration of the correction circuit 24' in FIG. 11 may be adopted. Further, in the case of applying to the case of the endoscope 2A or 2B in the following explanation, the above described configuration is assumed as the correction circuit 24. Note that the memory 23 in the endoscope 2A or 2B may adopt a configuration in which the defective pixel storage section 23c is not included in the memory 23 illustrated in FIG. 11.

In the present modification, as described as follows, in a plurality of frame periods in the second operation mode, the signal values of the black levels by the first operation mode are acquired, and correction of the black levels is enabled to be performed by using the acquired signal values. By performing correction like this, a case that the black levels vary for the reason of an ambient temperature in a case of performing endoscope inspection changing can be handled.

Note that the following explanation can be not only applied to the case of the endoscope 2C, but also can be applied to the case of the endoscope 2A or 2B.

That is, the case of the first embodiment is included. When supplementary explanation is further made, if application is made to the case of the endoscope 2A or 2B, the case where the black levels vary due to the ambient temperature in the case of performing endoscope inspection changing can be handled, and when application is made to the endoscope 2C, an effect of being able to correct a pixel defect is further added.

In the present modification, in the processing illustrated in FIG. 7, for example, after the processing in step S9, the control circuit 32 judges whether or not input of an instruction to acquire the signal values of the black levels by the first operation mode is performed from the operation panel 33 or the like during the second operation mode, as in step S31 illustrated by a dotted line.

The control circuit 32 shifts to processing in step S33 when input of the instruction is not performed, and when input of the instruction is performed, the control circuit 32 performs processing of acquiring the signal values of the black levels by the first operation mode during the second operation mode as illustrated in step S32. Subsequently, the signal values of the black levels in the memory 23 are updated. Accordingly, when correction of the black levels is performed by using the signal values of the black levels stored in the memory 23 after step S32 is performed, correction of the black levels is performed by using the signal values of the black levels which are updated in the processing in step S32.

Further, in step S33 next to step S32, the control circuit 32 judges whether or not input of an instruction to end (endoscope) inspection is performed, and when input of the instruction to end inspection is not performed, the flow returns to the processing in step S6, for example, and when the input of the instruction to end inspection is performed, the processing in FIG. 7 is ended.

Figure 13:
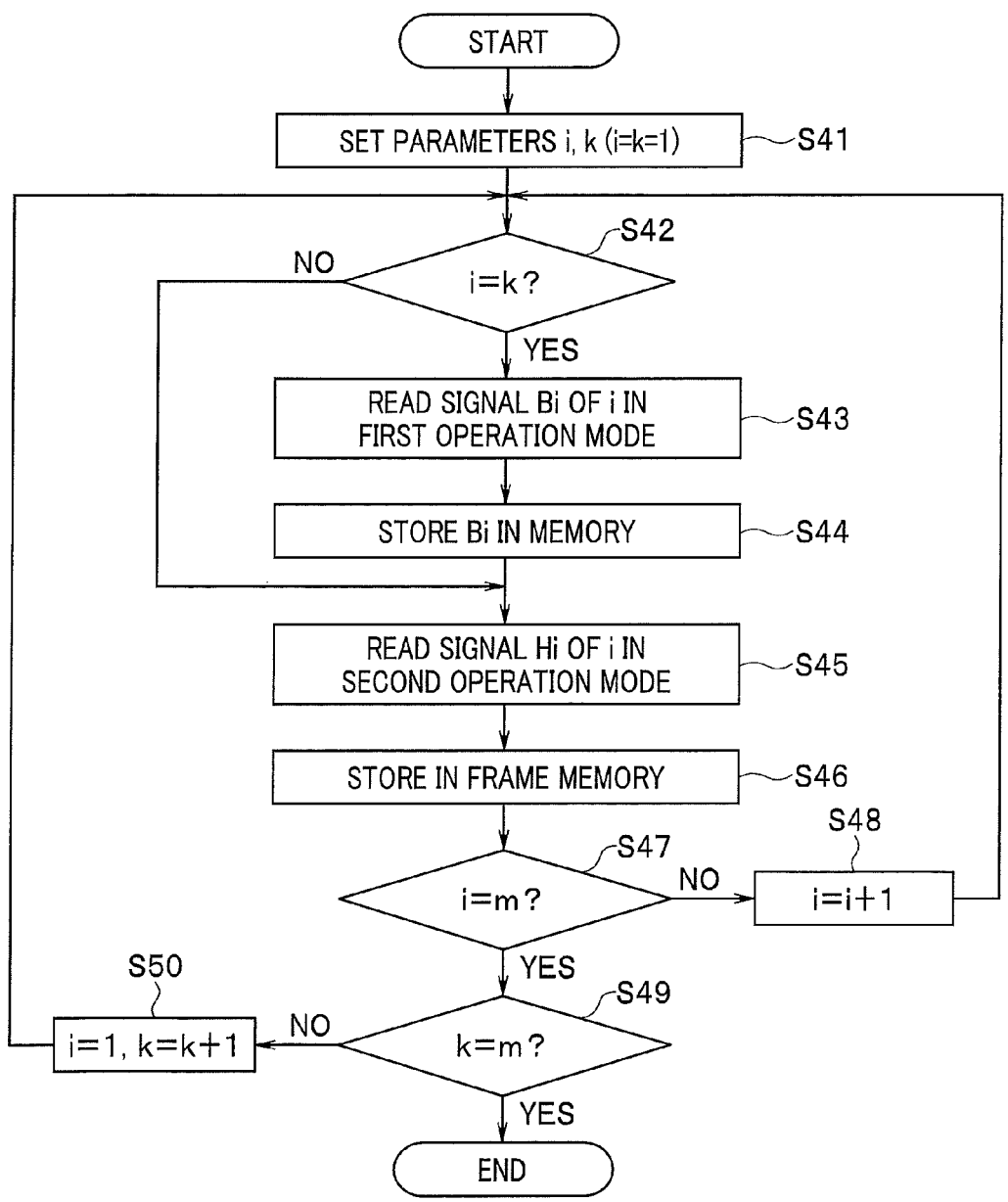
FIG. 13 is a flowchart illustrating a processing content for acquiring data of a black level by the first operation mode, during the second operation mode.

FIG. 13 illustrates the detailed processing in step S32. Note that in the following explanation, a plurality of pixels that form the light receiving section 45 are assumed to be disposed in a lattice shape along m and n lines (m and n are natural numbers of three or more) that are respectively provided in plurality along the horizontal direction (or a first direction) and the vertical direction (or a second direction) orthogonal to the horizontal direction.

Citing the configuration in FIG. 3, the above corresponds to a case in which two rows of pixels in FIG. 3 are changed to m rows and two columns of pixels are changed to n columns.

When the processing in FIG. 13 is started, in step S41, the imager operation control circuit 51 in the imager control circuit 22 (performing a control operation under control of the control circuit 32), for example, performs control so that the timing generator 53 sets parameters i and k in the case of driving the MOS type image pickup device 16 at initial values i=1 and k=1. In the following, explanation will be made in a case where the imager operation control circuit 51 also performs the operation controlled by the timing generator 53.

An outline of the processing illustrated in FIG. 13 shows that in a case where the operation timing is set so as to perform the first operation mode during the second operation mode by the setting section 33a or the like, the imager operation control circuit 51 that configures the operation mode control section reads the pixels of one line in the pixels of the m lines in the first operation mode, holds (or stores)

signals of the pixels of the one line which are read in the memory 23 as signal values of black levels, reads signals of the pixels of m lines in the second operation mode, holds (or stores) the signals of the pixels of m lines which are read in the frame memory 62a or 62b, and performs correction of the black levels before or after holding (or storing) the signals in the frame memory 62a or 62b.

Further, processing of acquiring signal values of the black levels of all the pixels in the light receiving section 45 is achieved by sequentially changing the pixels of one line which are read in the above described first operation mode from a first line to a last $m^{th}$ line, for example. After acquisition, the operation mode is the operation mode of performing only the second operation, and correction of an image signal obtained in the second operation mode is performed by using the signal values of the black levels acquired by the first operation mode.

The parameter i in step S41 described above expresses a parameter in the case of reading the signals (expressed by Hi) of the pixels of one line in the horizontal direction, the parameter k expresses a parameter in the case of reading the signals (expressed by Bk) of the black levels of the pixels of one line in the horizontal direction in the first operation mode.

In next step S42, the imager operation control circuit 51 judges whether the parameter i is equal to k. In the case of an initial value, the parameter i (=1) is equal to k (=1), and therefore, the flow goes to processing in next step S43. In step S43, the imager operation control circuit 51 performs control so that the reading section 46 reads a signal Bi (=Bk) of the parameter i in the first operation mode. That is, (the reset/transfer control circuit 43 of) the reading section 46 outputs the reset signal φR, and thereafter, reads the signal of the parameter i as the signal Bi of the black level in the first operation mode in which the transfer signal φT is turned off.

As illustrated in step S44, the signal Bi of the black level of the parameter i (=k=1) that is outputted from the MOS type image pickup device 16 is stored (held) in a second signal value storage section (illustrated by 23aa in FIG. 11) of the signal value storage section 23a of the memory 23 in such a manner that signal values corresponding to one line are sequentially stored (held) in a memory area corresponding to pixel addresses of the one line. In this case, the imager operation control circuit 51 switches the changeover switch 55 so that the contact point a is turned on.

In next step S45, the imager operation control circuit 51 performs control so that the reading section 46 reads the signal Hi of the parameter i in the second operation mode. That is, (the reset/transfer control circuit 43 of) the reading section 46 reads the signal Hi of the parameter i in the second operation mode in which the transfer signal φT is turned on after the reading section 46 outputs the reset signal φR.

As illustrated in step S46, as for the signal Hi of the parameter i (=1) which is outputted from the MOS type image pickup device 16, the image signal corresponding to one line is stored in the frame memory 62a or 62b of the correction circuit 24'. In this case, the imager operation control circuit 51 switches the changeover switch 55 so that the contact point b is turned on.

In next step S47, the imager operation control circuit 51 performs judgment of whether or not the parameter i is the last line m. Since the parameter i is 1 at present, the parameter i is judged as unequal to m, and after processing of increasing the parameter i by one (i=i+1) is performed in step S48, the flow goes to the processing in step S42. In this case, the parameter i becomes 2.

In step S42, the imager operation control circuit 51 judges that the parameter i (=2) is not equal to k(=1), and the flow goes to the processing in step S45. In step S45, the imager operation control circuit 51 performs control so that the signal Hi of the parameter i is read in the second operation mode, and after the imager operation control circuit 51 performs the processing in step S46 to S8 similarly to the case of the parameter i being 1, the flow returns to the processing in step S42.

When the parameter i becomes equal to m after the processing as above is repeated, read of the image corresponding to one frame is ended, the flow goes to processing in step S49 via the judgment processing in step S47.

In step S49, the imager operation control circuit 51 performs judgment of whether or not the parameter k is equal to m, and in a case of a judgment result of the parameter k being unequal to m, the imager operation control circuit 51 increases the parameter i by one, and increases the parameter k by one (k=k+1) in next step S50, and thereafter, the flow returns to the processing in step S42.

In this case, in step S42, the imager operation control circuit 51 judges that the parameter i (=1) is not equal to k (=2), goes to the processing in step S45, performs the processing in steps S45 to S48, and thereafter, returns to the processing in step S42.

In this case, the parameter i becomes two, and therefore it is judged that the parameter i is equal to k (=2) in step S42. Subsequently, the processing in steps S43 and S44 is performed, the processing in steps S45 to S48 is further performed, and the flow returns to the processing in step S42.

The processing as above is switched until the parameter k becomes equal to m. When the parameter k becomes equal to m, the processing of storing (holding) the signal values of the black levels of all the pixels in the light receiving section 45 in the second signal value storage section 23aa of the signal value storage section 23a in the memory 23 is ended.

Consequently, when the imager operation control circuit 51 judges that the parameter k is equal to m in step S49, the processing in FIG. 13 is ended.

When the processing in FIG. 13 is ended, the operation mode is the operation mode of performing only the second operation mode, correction of the black levels of the image signal in the second operation mode is performed by using the signal values of the black levels stored in the second signal value storage section 23aa by the processing in FIG. 13.

Note that in a period until the processing of storing the signal values of the black levels of all the pixels in the light receiving section 45 in the second signal value storage section 23aa illustrated in FIG. 13 is ended, the signal values of the black levels of all the pixels in the light receiving section 45 that are stored in the signal value storage section 23a in the memory 23 before the processing is ended can be used in correction of the black levels. Correction of the black levels is not limited to the above case, and when the signal values of the black levels that are already stored before the processing in FIG. 13 is started in the user signal value storage section 23aa are present, for example, the signal values of the old black levels are updated by the processing in FIG. 13, and correction of the black levels may be performed by using signal values of the black level some of which are updated.

According to the modification which operates in this way, even in a case where an ambient temperature at which the endoscope 2A, 2B or 2C is used changes, and the black levels change, the information on the black levels in the ambient temperature is acquired, and black levels of an image to be displayed on the monitor 5 can be corrected with high precision. Further, in the case of the endoscope 2C, a pixel defect can be also corrected.

Further, as for the processing illustrated in FIG. 13, with respect to an ordinary read period T for one frame in which signal reading for m lines is performed in the case of reading all the pixels in the light receiving section 45, a read period T for m+1 lines is T×(m+1)/m, and therefore in a case of m>>1, information on the black levels of all the pixels in the light receiving section 45 can be acquired by repeating substantially a same period as the ordinary read period T for an m frame period. Subsequently, after acquisition of the information on the black levels, an image with high quality can be displayed on the monitor 5 by using the acquired information on the black levels.

Note that as for the processing illustrated in FIG. 13, the case of processing of acquiring the signal values of the black levels corresponding to one line in the read period T for one frame is described, but processing of acquiring pixel signal values of black levels of a plurality of lines such as two lines or three lines may be performed.

Note that the processing illustrated in FIG. 13 may be changed. For example, when pixels of a $j^{th}$ line is read, as the information on the black levels in the first operation mode, for example, reading of no pixels of the $j^{th}$ line may be performed in the second operation mode. In this case, the pixels of the $j^{th}$ line in the second operation mode are omitted, so that (omission) may be corrected with signal values of pixels of both a $j-1^{th}$ line and a $j+1^{th}$ line that are adjacent to the single $j^{th}$ line, or (omission) may be corrected with pixels of the single $j^{th}$ line of the previous frame (the processing illustrated in FIG. 13 has a merit of being able to acquire an image of a moving image of one frame without requiring correction like this).

Further, in the aforementioned explanation, the example of acquiring the pixel signal values of black levels with respect to all the pixels forming the light receiving section 45 is described, but only one pixel signal value can be acquired with respect of each of the respective lines.

Note that the aforementioned embodiment including the modification may be partially combined and a different embodiment may be configured.

What is claimed is:

1. An image pickup apparatus, comprising:
   an endoscope provided with, at a distal end portion of an insertion portion, a solid state image pickup device including a plurality of pixels with, as a unit pixel, a photoelectric conversion element configured to perform photoelectric conversion corresponding to a light reception amount, and accumulate electric charges,
   a transfer section configured to transfer the electric charges accumulated in the photoelectric conversion element,
   an electric charge conversion section configured to convert the electric charges which are transferred, into a signal,
   a reset section configured to reset the signal of the electric charge conversion section,
   a signal output section configured to output the signal converted by the electric charge conversion section, and
   a vertical transfer line connected to the signal output section; and
   a signal processing apparatus including a setting section configured to set operation timings of a first operation mode of outputting a pixel signal of a black level as a result of a signal level of the electric charge conversion section being made the black level by bringing the reset section into an off state, and bringing the transfer section into an off state to the vertical transfer line, and a second operation mode of transferring the electric charges accumulated by the photoelectric conversion element to the electric charge conversion section by bringing the reset section into the off state from an on state, and bringing the transfer section into an on state, and thereafter outputting the signal of the electric charge conversion section to the vertical transfer line via the signal output section as an ordinary pixel signal in which a black level is not corrected,
   an operation mode control section configured to switch the first operation mode and the second operation mode, and
   a black level correction section configured to correct black levels in an image signal formed of the ordinary pixel signal in plurality that are outputted from an output section of the solid state image pickup device in the second operation mode,
   wherein the signal processing apparatus holds pixel signal values of black levels acquired in the first operation mode in a memory, and
   corrects the image signal acquired in the second operation mode in the black level correction section by using the pixel signal values of the black levels held in the memory, and
   the image pickup apparatus,
   as signal lines inserted through an inside of the insertion portion, and configured to transmit a synchronous signal for generating a drive signal for causing the image signal to be outputted from the solid state image pickup device, an operation mode control signal for causing the solid state image pickup device to operate in the first operation mode and the second operation mode respectively, and the image signal, transmits the synchronous signal and the operation mode control signal with use of a common signal line.

2. The image pickup apparatus according to claim 1, wherein the memory holds pixel signal values of black levels of all of the photoelectric conversion element in plurality that are outputted from the solid state image pickup device in the first operation mode, and
   the black level correction section corrects all the ordinary pixel signals configuring the image signal acquired by the second operation mode respectively in accordance with the pixel signal values of the black levels held in the memory.

3. The image pickup apparatus according to claim 1, wherein the endoscope includes a second memory that holds an address of a defective pixel in the solid state image pickup device contained in the endoscope, and
   the black level correction section makes correction with pixel signals of a plurality of pixels around the defective pixel, to the image signal corresponding to the address of the defective pixel in the second operation mode.

4. The image pickup apparatus according to claim 1, wherein in the solid state image pickup device, the plurality of pixels are disposed in a lattice shape along m and n lines that are respectively provided in plurality in a first direction and a second direction orthogonal to each other, and when the operation timing is set to perform the first operation mode during the second operation mode by the setting section, the operation mode control section performs control to repeatedly perform control of reading pixels of one line in pixels of m lines in the first operation mode, holding signals of the pixels of the one line which are read in the memory as signal values of black levels, and reading signals of the pixels of the m lines in the second operation mode by changing the one line in a case of reading in the first operation mode.

5. The image pickup apparatus according to claim 4, wherein the operation mode control section performs control so as to repeatedly perform control for m frame period by changing the one line from which the pixel signals are outputted from the solid state image pickup device by the first operation mode sequentially to different m lines for each frame period.

6. The image pickup apparatus according to claim 5, wherein the signal processing apparatus includes an image processing circuit configured to generate a display image signal to be displayed on a monitor with respect to an image signal formed of the signals of the pixels of the m lines that are read from the solid state image pickup device in the second operation mode, and the monitor displays an image of the display image signal having the pixels of m lines in the m frame period in which the operation mode control section performs control so as to repeatedly perform the control for the m frame period by changing the one line from which the pixel signals are outputted from the solid state image pickup device by the first operation mode sequentially to different m lines for each frame period.

7. The image pickup apparatus according to claim 1, wherein the endoscope contains the memory configured to hold the pixel signal values of the black levels acquired in the first operation mode with respect to the solid state image pickup device provided in the endoscope, and the black level correction section configured to make correction by using the pixel signal values of the black levels held in the memory.

* * * * *